US010112898B2

(12) United States Patent
Dwivedi et al.

(10) Patent No.: US 10,112,898 B2
(45) Date of Patent: *Oct. 30, 2018

(54) PROCESS FOR THE PREPARATION OF SAROGLITAZAR PHARMACEUTICAL SALTS

(71) Applicant: Cadila Healthcare Ltd., Ahmedabad, Gujarat (IN)

(72) Inventors: Shri Prakash Dhar Dwivedi, Gujarat (IN); Ramesh Chandra Singh, Gujarat (IN); Jagdish Maganlal Patel, Gujarat (IN); Vikas Patel, Gujarat (IN); Vishwadeepak Rama Pati Tripathi, Gujarat (IN); Pranav Jitendra Gangwar, Gujarat (IN); Jigar Mukundbhai Raval, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/916,402

(22) PCT Filed: Sep. 5, 2014

(86) PCT No.: PCT/IN2014/000584
§ 371 (c)(1),
(2) Date: Mar. 3, 2016

(87) PCT Pub. No.: WO2015/033357
PCT Pub. Date: Mar. 12, 2015

(65) Prior Publication Data
US 2016/0194280 A1 Jul. 7, 2016

(30) Foreign Application Priority Data
Sep. 6, 2013 (IN) .......................... 2905/MUM/2013

(51) Int. Cl.
C07D 207/333 (2006.01)
C07D 207/32 (2006.01)

(52) U.S. Cl.
CPC ....... C07D 207/333 (2013.01); C07D 207/32 (2013.01)

(58) Field of Classification Search
CPC .......................... C07D 207/32; C07D 207/333
See application file for complete search history.

(56) References Cited

U.S. PATENT DOCUMENTS

| 4,231,938 | A | 11/1980 | Monaghan et al. |
| 4,346,227 | A | 8/1982 | Terahara et al. |
| 4,444,784 | A | 4/1984 | Hoffman et al. |
| 5,273,995 | A | 12/1993 | Roth |
| 5,354,772 | A | 10/1994 | Kathawala |
| 6,166,063 | A | 12/2000 | Villhauer |
| 6,395,767 | B2 | 5/2002 | Robl et al. |
| 6,699,871 | B2 | 3/2004 | Edmondson et al. |
| 6,987,123 | B2 | 1/2006 | Lohray et al. |
| 6,987,132 | B1 | 1/2006 | Lohray et al. |
| 7,041,837 | B2 | 5/2006 | Lohray et al. |
| 7,323,491 | B2 | 1/2008 | Lohray et al. |
| 7,407,955 | B2 | 8/2008 | Himmelsbach et al. |
| 8,110,598 | B2 | 2/2012 | Lohray et al. |
| 8,212,057 | B2 | 7/2012 | Lohray et al. |
| 8,558,009 | B2 | 10/2013 | Lohray et al. |
| 8,772,342 | B2 | 7/2014 | Darteil et al. |
| 2003/0199498 | A1 | 10/2003 | Lohray et al. |
| 2003/0236254 | A1* | 12/2003 | Lohray .............. C07D 207/325 514/227.8 |
| 2007/0238776 | A1 | 10/2007 | Lohray et al. |
| 2009/0196923 | A1 | 8/2009 | Mandal et al. |
| 2011/0275669 | A1 | 11/2011 | Lohray et al. |
| 2012/0121729 | A1 | 5/2012 | Paterson et al. |
| 2013/0338209 | A1 | 12/2013 | Gambhire et al. |
| 2016/0068484 | A1 | 3/2016 | Jain et al. |
| 2016/0107989 | A1 | 4/2016 | Dwivedi et al. |
| 2016/0136131 | A1 | 5/2016 | Patel et al. |
| 2016/0166539 | A1 | 6/2016 | Patel et al. |
| 2016/0194280 | A1 | 7/2016 | Dwivedi et al. |
| 2016/0207884 | A1 | 7/2016 | Dwivedi et al. |

FOREIGN PATENT DOCUMENTS

| EP | 1586571 A1 | 10/2005 |
| IN | 1910/MUM/2013 A | 5/2013 |
| WO | WO-91/19702 A1 | 12/1991 |
| WO | WO-94/01420 A1 | 1/1994 |
| WO | WO-94/13650 A1 | 6/1994 |
| WO | WO-95/03038 A1 | 2/1995 |
| WO | WO-95/17394 A1 | 6/1995 |
| WO | WO-96/04260 A1 | 2/1996 |
| WO | WO-96/04261 A1 | 2/1996 |
| WO | WO-96/33998 A1 | 10/1996 |
| WO | WO-97/25042 A1 | 7/1997 |
| WO | WO-97/36579 A1 | 10/1997 |
| WO | WO-99/08501 A2 | 2/1999 |
| WO | WO-99/16758 A1 | 4/1999 |
| WO | WO-99/19313 A1 | 4/1999 |
| WO | WO-99/20614 A1 | 4/1999 |
| WO | WO-00/23417 A1 | 4/2000 |
| WO | WO-00/23445 A1 | 4/2000 |
| WO | WO-00/23451 A1 | 4/2000 |
| WO | WO-01/53257 A2 | 7/2001 |
| WO | WO-02/24625 A2 | 3/2002 |

(Continued)

OTHER PUBLICATIONS

Choi, International Journal of Mineral Processing vol. 74, Supplement 1, Dec. 10, 2004, pp. S165-S172.*

(Continued)

Primary Examiner — Valerie Rodriguez-Garcia
(74) Attorney, Agent, or Firm — Goodwin Procter LLP

(57) ABSTRACT

The present invention relates to an improved process for the preparation of pyrroles derivatives having hypolipidemic and hypocholesteremic activities. In particular, the invention relates to an improved process for the preparation of 2-ethoxy-3-(4-(2-(2-methyl-5-(4-(methylthio)phenyl)-1H-pyrrol-1-yl)ethoxy)phenyl)propanoate and its pharmaceutically acceptable salts, hydrates, solvates, polymorphs or intermediates thereof. The invention also relates to an improved process for the preparation of mesylate compound (A1).

20 Claims, 3 Drawing Sheets

(56) References Cited

FOREIGN PATENT DOCUMENTS

Figure 1:
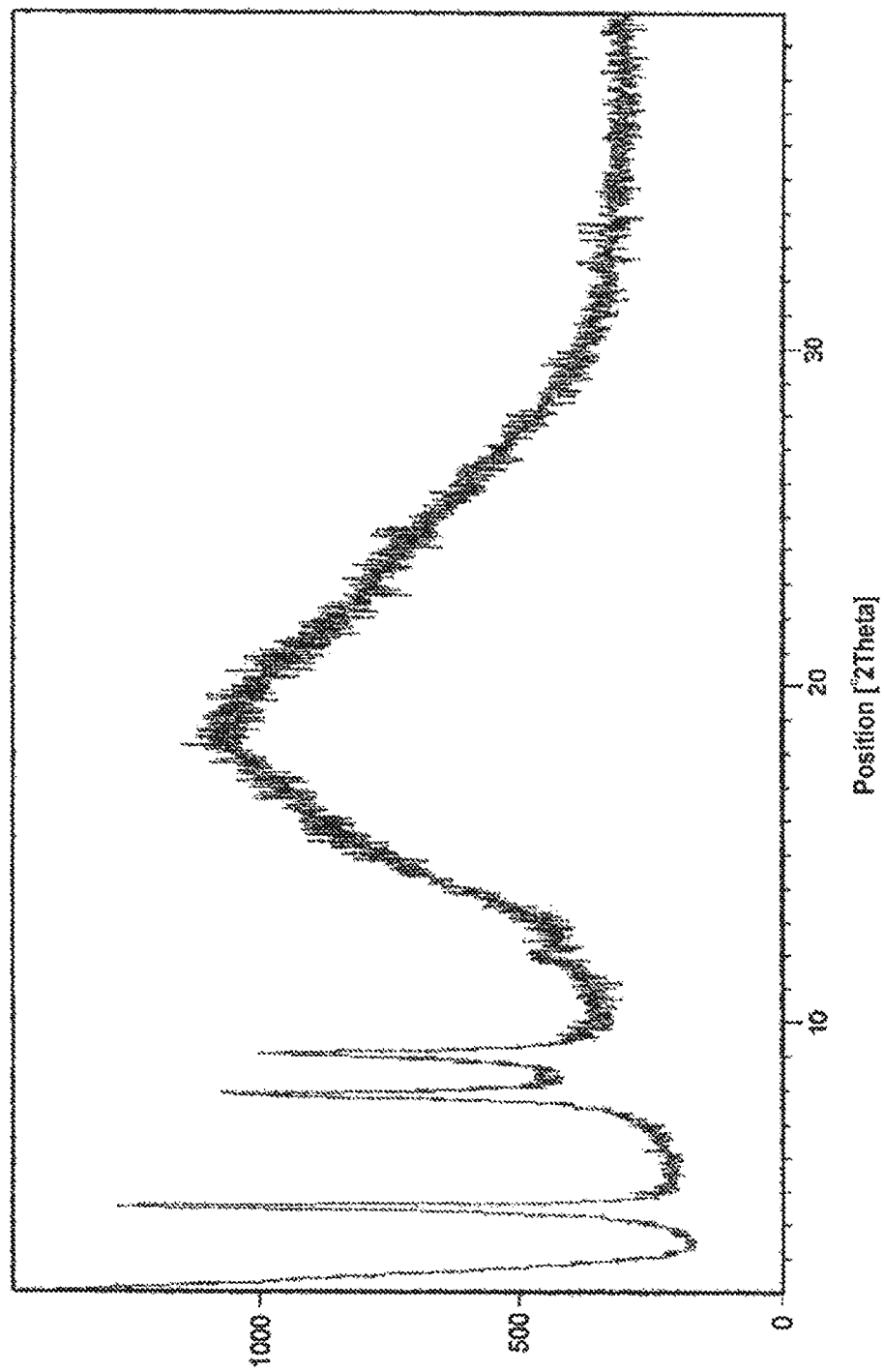

| WO | 2003/009841 A1 | 2/2003 |
| WO | WO-2005/031335 A1 | 4/2005 |
| WO | 2012/104869 A1 | 8/2012 |
| WO | WO2012/104869 * | 8/2012 |
| WO | WO-2014/174524 A1 | 10/2014 |
| WO | 2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |

OTHER PUBLICATIONS

Chaumeil, J.C., Methods and Findings in Experimental and Clinical Pharmacology, Apr. 1998, vol. 20, No. 3, pp. 211-215.*
Arnett (J. Am. Chem. Soc., 1965, 87 (7), pp. 1541-1553).*
International Search Report and Written Opinion dated Mar. 23, 2015 for Application No. PCT/IN2014/000584 (14 pages).
International Search Report and Written Opinion dated Feb. 2, 2015 for International Patent Application No. PCT/IN2014/000367 (14 pages).
Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" Clin. Drug Investig. (2013) vol. 33, pp. 809-816.
Brenna, E. et al. "Enzyme-mediated synthesis of EEHP and EMHP, useful pharmaceutical intermediates of PPAR agonists" Tetrahedron: Asymmetry (2009) vol. 20, pp. 2594-2599.
International Search Report and Written Opinion dated Dec. 19, 2014 for Application No. PCT/IN2014/000551 (11 pages).
Demuth, H.-U. et al. "Type 2 diabetes—Therapy with dipeptidyl peptidase IV inhibitors," Biochim. Biophys. Acta, 1751 (2005) pp. 33-44.
Augustyns, K. et al. "Inhibitors of proline-specific dipeptidyl peptidases: DPP IV inhibitors as a novel approach for the treatment of Type 2 diabetes," Expert Opin. Ther. Patents, (2005) vol. 15, No. 10, pp. 1387-1407.
Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (PRESS V)." J. Diabetes Sci. Technol. (2014) vol. 8, No. 1, pp. 132-141.
Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (PRESS VI)," Diabetes Technology & Therapeutics, (2014) vol. 16, No. 2, pp. 63-71.
International Search Report and Written Opinion dated Dec. 23, 2014 for International Patent Application No. PCT/IN2014/000445 (10 pages).
International Preliminary Report on Patentability dated Oct. 6, 2015 for International Patent Application No. PCT/IN2014/000445 (7 pages).
Ansel et al. "Pharmaceutical Dosage Forms and Drug Delivery Systems, Seventh Edition" 1999, pp. 88-92.
Cairns, D. (editor) "Essentials of Pharmaceutical Chemistry, Fourth Edition" 2012, p. 14.
Bharate, S. et al. "Interactions and incompatibilities of pharmaceutical excipients with active pharmaceutical ingredients: a comprehensive review." J. Excipient and Food Chem. (2010) vol. 1, No. 3, pp. 3-26.
International Search Report and Written Opinion dated Nov. 20, 2014 for International Application No. PCT/IN2014/000489 (10 pages).
International Preliminary Report on Patentability dated Oct. 9, 2015 for International Application No. PCT/IN2014/000489 (7 pages).
Response to Written Opinion filed May 21, 2015 for International Application No. PCT/IN2014/000489 (6 pages).
"Sodium Stearyl Fumarate", obtained on Jun. 23, 2015. Retrieved from the Internet: <URL: https://www.medicinescomplete.com/me/excipients/current/ . . . >, 4 pages.
Lieberman, et al. "Pharmaceutical Dosage Forms: Tablets, vol. 1, 2nd Edition" (1989) Marcel Dekker Inc., pp. 111-114.
Gennaro et al. "Remington's Pharmaceutical Sciences, 19th Edition" (1995) Mack Publishing, pp. 1380-1383.
Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.
International Search Report and Written Opinion dated Nov. 20, 2013 for International Application No. PCT/IN2013/000391 (13 pages).
International Preliminary Report on Patentability dated Jul. 9, 2015 for International Application No. PCT/IN2013/000391 (9 pages).
IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).
Anonymous "IND Minutes draft 19 07 12" Retrieved on Oct. 15, 2013 from the Internet from URL: http://www.docstoc.com/docs/145152750/IND-Minutes-draft-19-07-12 (1 page).
Anonymous "Lipaglyn™ Discovery, Development & Preclinical Studies" Retrieved on Oct. 15, 2013 from the Internet from URL: http://webcache.googleusercontent.com/search?q=cache:RGrhmYOHM3sJ:lipaglyn.com/downloads/Lipaglyn_Preclinical_Studies.ppsx (25 pages).
Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," Diabetes (2009) vol. 58, No. Suppl. 1, p. A569.
Ramirez, T. et al. "Structural Correlates of PPAR Agonist Rescue of Experimental Chronic Alcohol-Induced Steatohepatitis," J. Clin. Exper. Pathology (2012) vol. 2, No. 4, pp. 1-9.
Seo, Y. S. et al. "PPAR agonists treatment is effective in a nonalcoholic fatty liver disease animal model by modulating fatty-acid metabolic enzymes" J. Gatroenterology Hepatology (2008) vol. 23, No. 1, pp. 102-109.
Barb et al. (2016) "Pharmacological management of nonalcoholic fatty liver disease" Metabolism Clinical and Experimental 65:1183-1195.
Berger et al. (2005) "PPARs: Therapeutic targets for metabolic disease" TRENDS in Pharmacological Sciences 26(5): 244-251.
Chou et al. (2013) "Metrelepin: First Global Approval" Drugs 73:989-997.
Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.
FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).
Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Package Insert for ACTOS (pioglitazone) tablets for oral use (2013).
Package Insert for AVANDIA (rosiglitazone maleate) Tablets (2008).
Palomer et al. (2016) "PPARβ/δ and lipid metabolism in the heart" Biochemica et Biophysica Acta 1861:1569-1578.
Yessoufou et al. (2010) "Multifaceted roles of peroxisome proliferator-activated receptors (PPARs) at the cellular and whole organism levels" Swiss Medical Weekly 140:w13071.

(56) References Cited

OTHER PUBLICATIONS

International Search Report dated May 9, 2012 for International Application No. PCT/IN2012/000069 (3 pages).
van Wijk, J. P. H. et al. "Comparison of Rosiglitazone and Metformin for Treating HIV Lipodystrophy: A Randomized Trial," *Ann. Internal Med.* (2005) vol. 143, No. 5, pp. 337-346.
Hadigan, C. et al. "Metabolic Effects of Rosiglitazone in HIV Lipodystrophy: A Randomized, Controlled Trial," *Ann. Internal Med.* (2004) vol. 140, No. 10, pp. 788-794. (Abstract Only).
Macallan, D. C. et al. "Treatment of Altered Body Composition in HIV Associated Lipodystrophy: Comparison of Rosiglitazone, Pravastatin, and Recombinant Human Growth Hormone," *HIV Clinical Trials*, (2008) vol. 9, Issue 4, pp. 254-268. (Abstract Only).
Tungsiripat, M. et al. "Rosiglitazone improves lipoatrophy in patients receiving thymidine-sparing regimens," *AIDS*, (2010) vol. 24, pp. 1291-1298.
Fan, W. and Evans, R. "PPARs and ERRs: molecular mediators of mitochondrial metabolism" *Curr. Opin. Cell Bio.* (2015) vol. 33, pp. 49-54.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
International Preliminary Report on Patentability dated Aug. 15, 2013 for International Application No. PCT/IN2012/000069 (5 pages).
International Preliminary Report on Patentability dated Dec. 1, 2015 for International Patent Application No. PCT/IN2014/000367 (9 pages).
International Preliminary Report on Patentability dated Mar. 1, 2016 for Application No. PCT/IN2014/000551 (7 pages).
Written Opinion of the International Searching Authority dated May 9, 2012 for International Application No. PCT/IN2012/000069 (4 pages).
Pharmatrans Sanaq AG "LubriSanaq®—Sodium Stearyl Fumarate" dated Feb. 5, 2008. Retrieved on Jan. 23, 2017 from the Internet at URL: http:www.pharmaceutical-technology.com/contractors/excipients/pharmatrans-sanaq/press9.html. (2 pages).
U.S. Appl. No. 13/978,791, Treatment for Lipodystrophy, filed Jul. 9, 2013.
U.S. Appl. No. 15/345,035, Treatment for Lipodystrophy, filed Nov. 7, 2016.
U.S. Appl. No. 14/782,609, A Novel Composition for Nonalcoholic Fatty Liver Disease (NAFLD), filed Oct. 6, 2015.
U.S. Appl. No. 15/343,859, A Novel Composition for Nonalcoholic Fatty Liver Disease (NAFLD), filed Nov. 4, 2016.
U.S. Appl. No. 14/899,912, Formula Comprising a Hypolipidemic Agent, filed Dec. 18, 2015.
U.S. Appl. No. 14/783,336, Synergistic Compositions, filed Oct. 8, 2015.
U.S. Appl. No. 14/894,744, A Process for Preparation of Pyrroles Having Hypolipidemic Hypocholesteremic Activities, filed Nov. 30, 2015.
U.S. Appl. No. 15/366,229, A Process for Preparation of Pyrroles Having Hypolipidemic Hypocholesteremic Activities, filed Dec. 1, 2016.
U.S. Appl. No. 14/915,457, Polymorphic Form of Pyrrole Derivative and Intermediate Thereof, filed Feb. 29, 2016.
International Preliminary Report on Patentability dated Mar. 8, 2016 for Application No. PCT/IN2014/000584.

\* cited by examiner

PROCESS FOR THE PREPARATION OF SAROGLITAZAR PHARMACEUTICAL SALTS

RELATED APPLICATION

This application is a national phase entry under 35 USC 371 of International Patent Application No.: PCT/IN2014/000584 filed on 05 Sep. 2014, which claims priority from Indian Application No, 2905/MUM/2013 filed on 06 Sep. 2013, the disclosures of which are incorporated in their entirety by reference herein.

FIELD OF THE INVENTION

The present invention relates to an improved process for the preparation of pyrroles derivatives having hypolipidemic and hypocholesteremic activities. In particular, the invention relates to an improved process for the preparation of 2-ethoxy-3-(4-(2-(2-methyl-5-(4-(methylthio)phenyl)-1H-pyrrol-1-yl)ethoxy)phenyl)propanoate and its pharmaceutically acceptable salts, hydrates, solvates, polymorphs or intermediates thereof. The invention also relates to an improved process for the preparation of mesylate compound (A1).

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Pyrrole derivative of present invention is chemically 2-ethoxy-3-(4-(2-(2-methyl-5-(4-(methylthio)phenyl)-1H-pyrrol-1-yl)ethoxy)phenyl)propanoate, which may be optically active or racemic and its pharmaceutically acceptable salts, hydrates, solvates, polymorphs or intermediates thereof. The INN name for pyrrole derivative is Saroglitazar® which is magnesium salt of pyrrole compound of Formula (I), having below chemical structure.

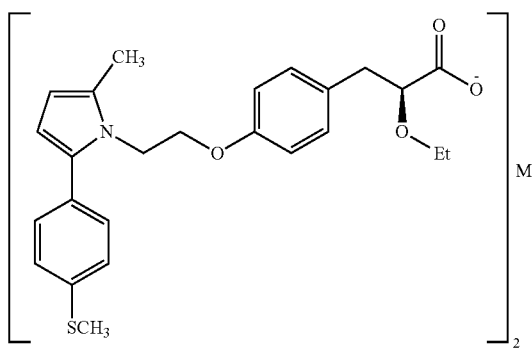

The compound of Formula (I) lower or modulate triglyceride levels and/or cholesterol levels and/or lower density lipoproteins (LDL) and raise HDL plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions. The compound of Formula (I) are useful to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

U.S. Pat. No. 6,987,123 B2 (the US '123 patent) discloses novel heterocyclic compounds, their preparation, pharmaceutical compositions containing them and their use in medicine. The US '123 patent discloses five reaction pathways for the synthesis of pyrrole derivatives.

In route-1 the compound of Formula (1a) and (1b) are reacted under Paal-Knoor conditions to obtain compound (1) as shown below:

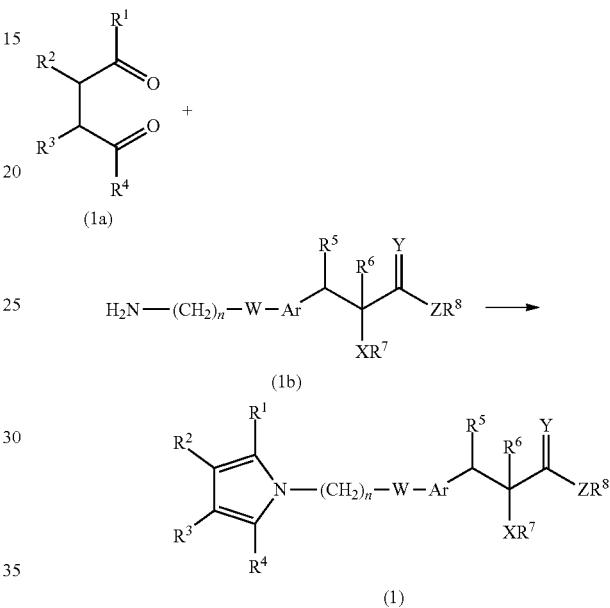

In route-2 the compound of Formula (1c) and (1d) are reacted in presence of base in suitable organic solvent to obtain the compound (1) as shown below:

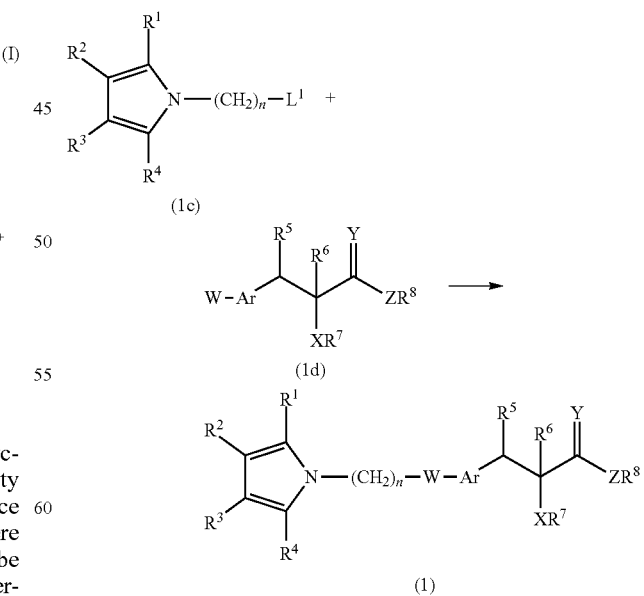

In route-3 the compound of Formula (1e) and (1d) are reacted in presence of coupling agents like DCC, EDC etc. to obtain the compound (1) as shown below:

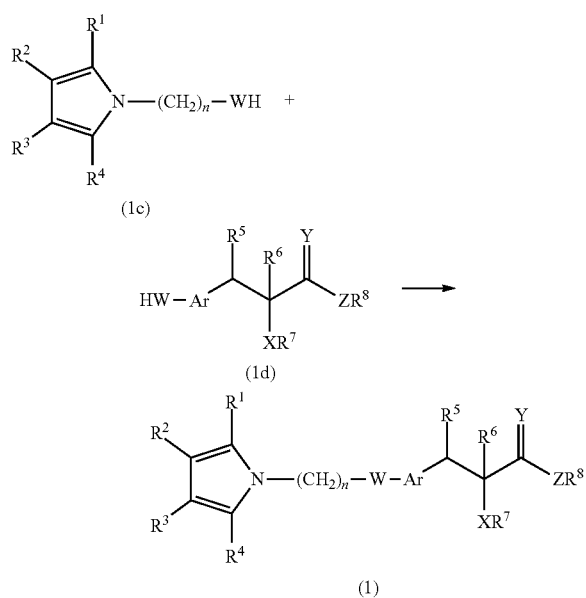

(1c)

(1d)

(1)

In route-4 the compound of Formula (1f) and (1g) are reacted in presence of rhodium salts such as rhodium (II) acetate in suitable solvents like benzene, toluene, ether, THF, dioxane and the like to obtain the compound (1) as shown below:

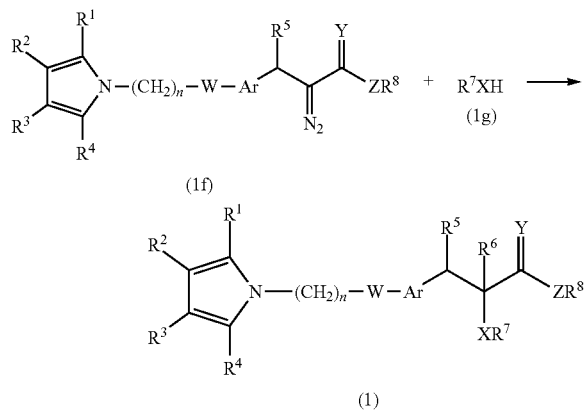

(1f)

(1g)

(1)

In route-5 the compound of Formula (1e) and (1d) are reacted under Wittig Homer conditions to obtain the compound (1) as shown below:

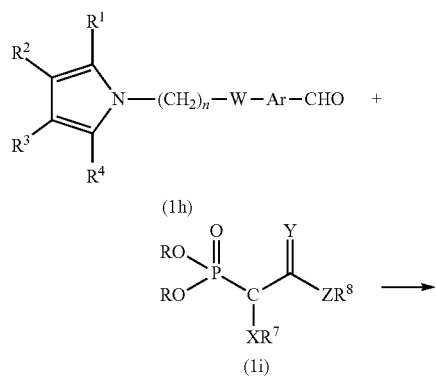

(1h)

(1i)

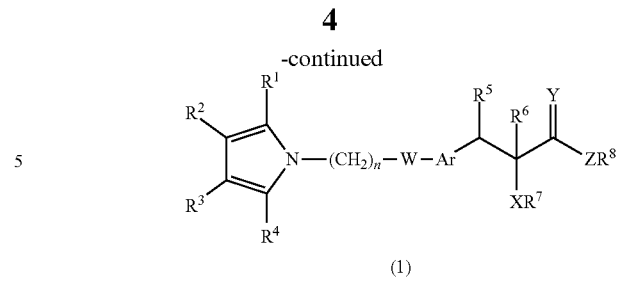

(1)

U.S. Pat. Nos. 7,041,837 B2, 7,323,491 B2, 8,110,598 B2, 8,212,057 B2 discloses different pyrrole derivative of Formula (1) and their intermediates.

U.S. PG-Pub. No. 2011/0275669 A1 discloses the process for the preparation of pyrrole derivative of general Formula (1) prepared by the five reaction pathways as disclosed herein above.

International (PCT) publication WO 2012/104869 A1 provides the use of compound of Formula (I) for the treatment of lipodystrophy.

Our own copending application IN 1910/MUM/2013 A discloses substantially amorphous saroglitazar magnesium having percentage crystallinity less than 25% and process for its preparation, which is incorporated herein as reference.

International (PCT) publication WO 2012/104869 A1 provides the use of compound of Formula (1) for the treatment of lipodystrophy.

The different physical properties exhibited by polymorphs affect important pharmaceutical parameters selected from storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e. g., tablets crumble on storage as a kinetically favored crystalline form converts to thermodynamically more stable crystalline form) or both (e. g., tablets of one polymorph are more susceptible to breakdown at high humidity). Solubility differences between polymorphs may, in extreme situations, result in transitions to crystalline forms that lack potency or are toxic. In addition, the physical properties of the crystalline form to that of an amorphous form may be important in pharmaceutical processing. For example, an amorphous form may provide better bioavailability than the crystalline form. Thus, a pt sent amorphous form may be useful for formulations which can have better stability, solubility, storage, compressibility etc important for formulation and product manufacturing and doesn't degrade to crystalline forms of saroglitazar.

Therefore, it is desirable to have an amorphous form of drugs with high purity to meet the regulatory requirements and also highly reproducible processes for their preparation.

In view of the above, it is therefore, desirable to provide an efficient, more economical, less hazardous and eco-friendly process for the preparation of substantially amorphous saroglitazar. However, the present amorphous form of saroglitazar may provide at least a suitable alternative for development of finished formulations.

SUMMARY OF THE INVENTION

In one general aspect, there is provided an improved process for the preparation of saroglitazar or its pharmaceutically acceptable salts of Formula (IB), (IB)

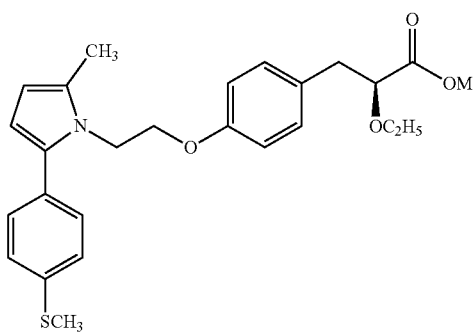

wherein M is hydrogen or a pharmaceutically acceptable cation, the process comprising:
(a) reacting a hydroxy compound (A) with a mesylate compound (A1) to obtain alkoxy ester compound of Formula (II);

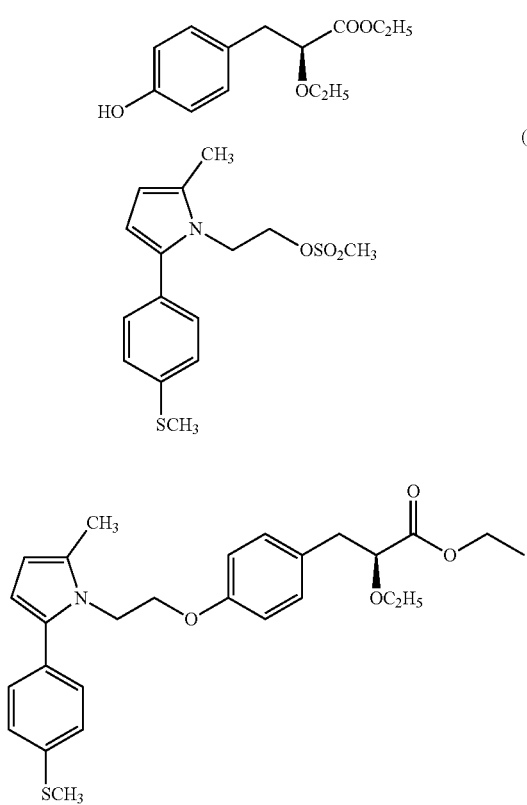

(b) hydrolyzing the alkoxy ester compound of Formula (II) to obtain a compound of Formula (IB);

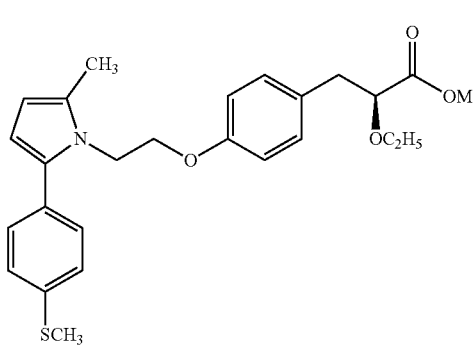

wherein M is hydrogen or a pharmaceutically acceptable cation;
(c) optionally, neutralizing the compound of Formula (IB), wherein M is a pharmaceutically acceptable cation to obtain a compound of Formula (IB), wherein M is hydrogen; and
(d) optionally, converting the compound of Formula (IB), wherein M is hydrogen to another compound of Formula (IB), wherein M is a pharmaceutically acceptable cation.

In another general aspect, there is provided an improved process for the preparation of saroglitazar magnesium of Formula (I), (I)

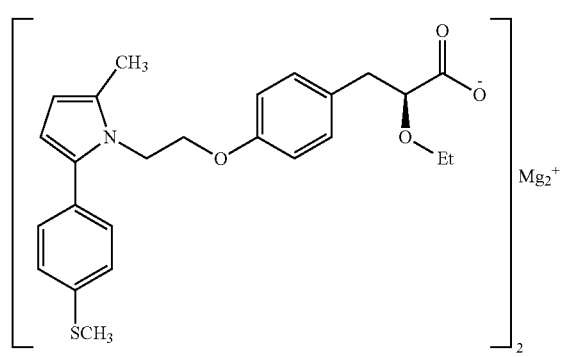

the process comprising:
(a) reacting a hydroxy compound (A) with a mesylate compound (A1) to obtain alkoxy ester compound of Formula (II);

(A)

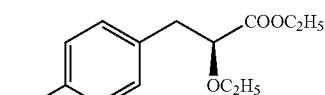

(A1)

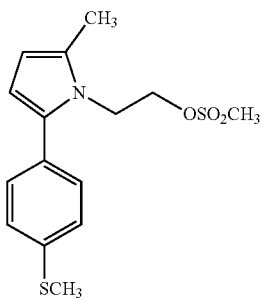

(II)

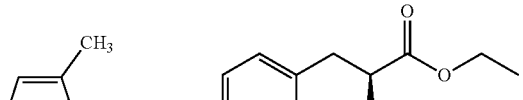

(b) hydrolyzing the alkoxy ester compound of Formula (II) to obtain a compound of Formula (IB);

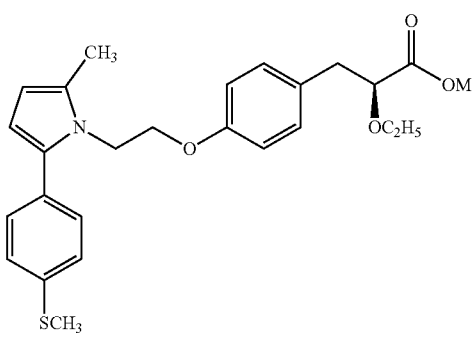

(IB)

wherein M is hydrogen or a pharmaceutically acceptable cation selected from sodium (Na), potassium (K), lithium (Li), calcium (Ca), barium (Ba), strontium (Sr) and zinc (Zn);

(c) optionally, neutralizing the compound of Formula (IB), wherein M is a pharmaceutically acceptable cation to obtain a compound of Formula (IB), wherein M is hydrogen; and (d) reacting the compound of Formula (IB), wherein M is hydrogen with a magnesium source to obtain the saroglitazar magnesium of Formula (I).

In another general aspect, there is provided an improved process for the preparation of saroglitazar magnesium of Formula (I),

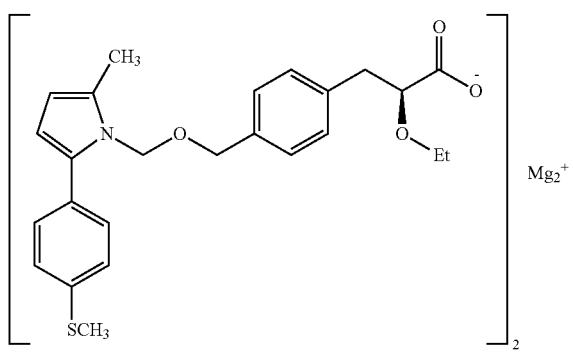

(I)

the process comprising:

(a) reacting a hydroxy compound (A) with a mesylate compound (A1) to obtain alkoxy ester compound of Formula (II);

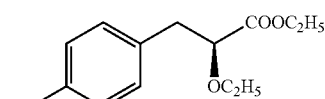

(A)

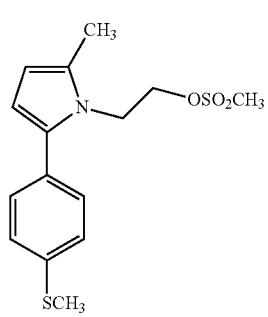

(A1)

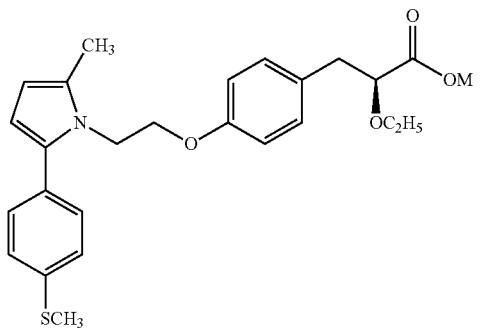

(II)

(b) hydrolyzing the alkoxy ester compound of Formula (II) with a base to obtain a compound of Formula (IB);

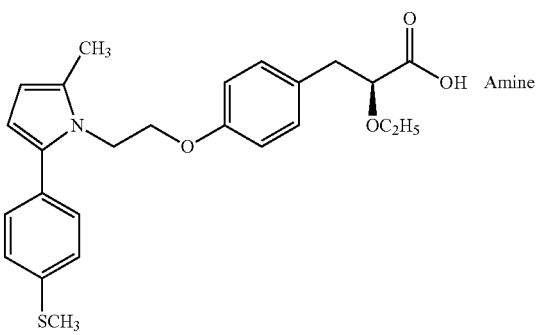

(IB)

wherein M is hydrogen or a pharmaceutically acceptable cation selected from sodium (Na), potassium (K), lithium (Li), calcium (Ca), barium (Ba), strontium (Sr) and zinc (Zn);

(c) optionally, neutralizing the compound of Formula (IB), wherein M is a pharmaceutically acceptable cation to obtain a compound of Formula (IB), wherein M is hydrogen; and (d) optionally, reacting the compound of Formula (IB), wherein M is hydrogen with an organic amine to obtain a compound of Formula (IC); and (IC)

(e) converting the compound of Formula (IC) to compound of Formula (IB), wherein M is hydrogen; and (f) reacting the compound of Formula (IB), wherein M is hydrogen with a magnesium source to obtain the saroglitazar magnesium of Formula (I).

In another general aspect, there is provided a process for the preparation of saroglitazar magnesium of Formula (I),

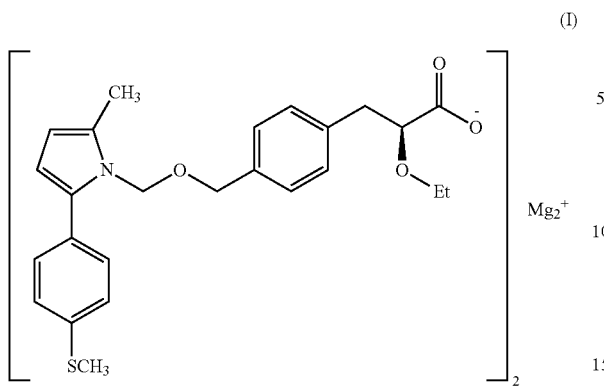

the process comprising:
(a) reacting 2-bromo-1-(4-(methylthio)phenyl)ethanone (E1) with methyl acetoacetate in one or more of organic solvents in the presence of a base to obtain a compound (D1);

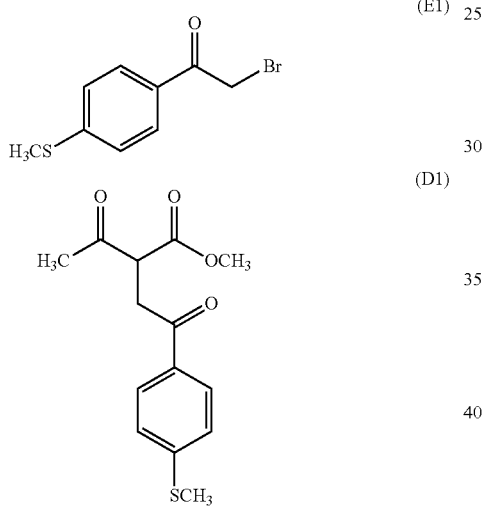

(b) hydrolyzing the compound (D1) in-situ with a base followed by decarboxylation to obtain the compound (C1);

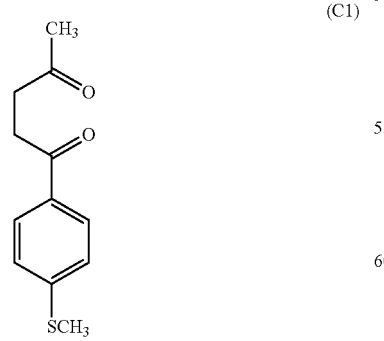

(c) reacting the compound (C1) in-situ with ethanolamine under Paal-Knoor conditions in the presence of an acid to obtain the compound (B1);

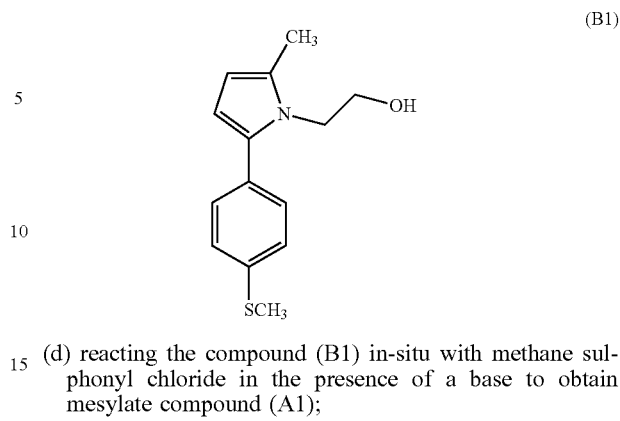

(d) reacting the compound (B1) in-situ with methane sulphonyl chloride in the presence of a base to obtain mesylate compound (A1);

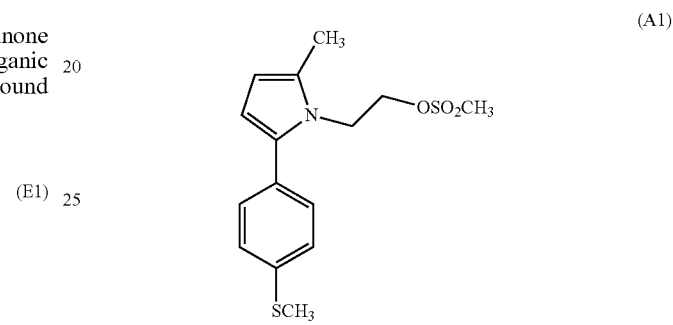

(e) reacting the mesylate compound (A1) in-situ with a hydroxy compound (A) in the presence of base to obtain an alkoxy ester compound of Formula (II);

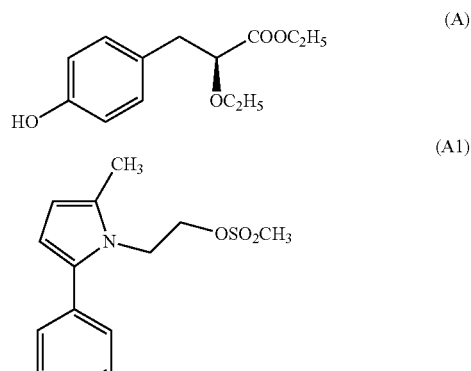

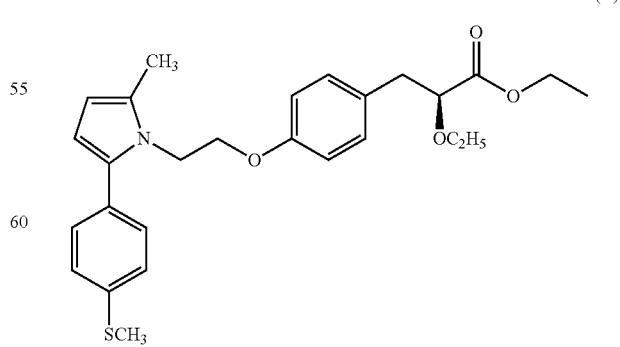

(f) hydrolyzing the alkoxy ester compound of Formula (II) in-situ to obtain a compound of Formula (IB);

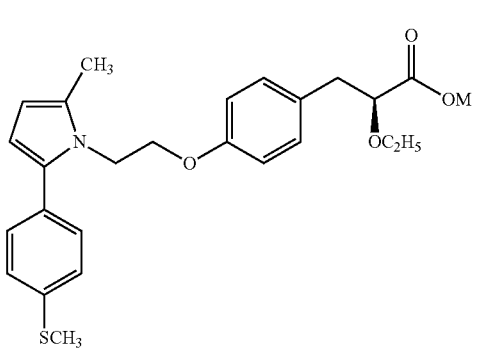

(IB)

wherein M is hydrogen or a pharmaceutically acceptable cation selected from sodium (Na), potassium (K), lithium (Li), calcium (Ca), barium (Ba), strontium (Sr) and zinc (Zn);

(g) optionally, neutralizing the compound of Formula (IB), wherein M is a pharmaceutically acceptable cation to obtain the compound of Formula (IB), wherein M is hydrogen; and (h) reacting the compound of Formula (IB), wherein M is hydrogen with a magnesium source to obtain the saroglitazar magnesium of Formula (I), wherein the process does not involve isolation of intermediates.

In another general aspect, there is provided an improved process for the preparation of mesylate compound of Formula (A1),

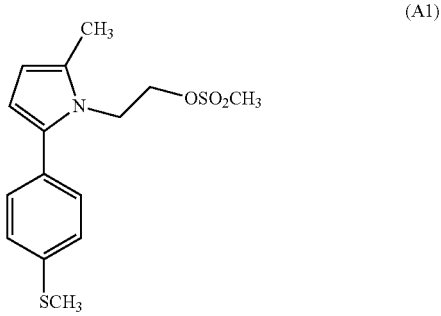

(A1)

the process comprising:
(a) reacting 4-(methylthio)benzaldehyde and methylvinylketone in the presence of a base and a stetter catalyst to obtain compound (C1);

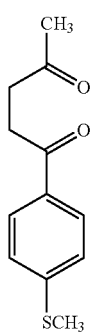

(C1)

(b) reacting the compound (C1) with ethanolamine under Paal-Knoor conditions in the presence of an acid to obtain compound (B1);

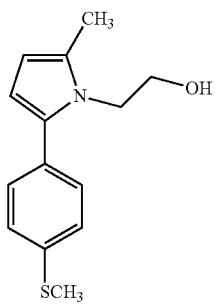

(B1)

(c) reacting the compound (B1) with methane sulphonyl chloride in the presence of a base in one or more of organic solvents to obtain the mesylate compound (A1); and (d) optionally, purifying the mesylate compound of Formula (A1).

BRIEF DESCRIPTION OF THE ACCOMPANYING DRAWINGS

FIG. 1 discloses the x-ray diffractogram (XRD) of the substantially amorphous form of saroglitazar magnesium.

Figure 2:
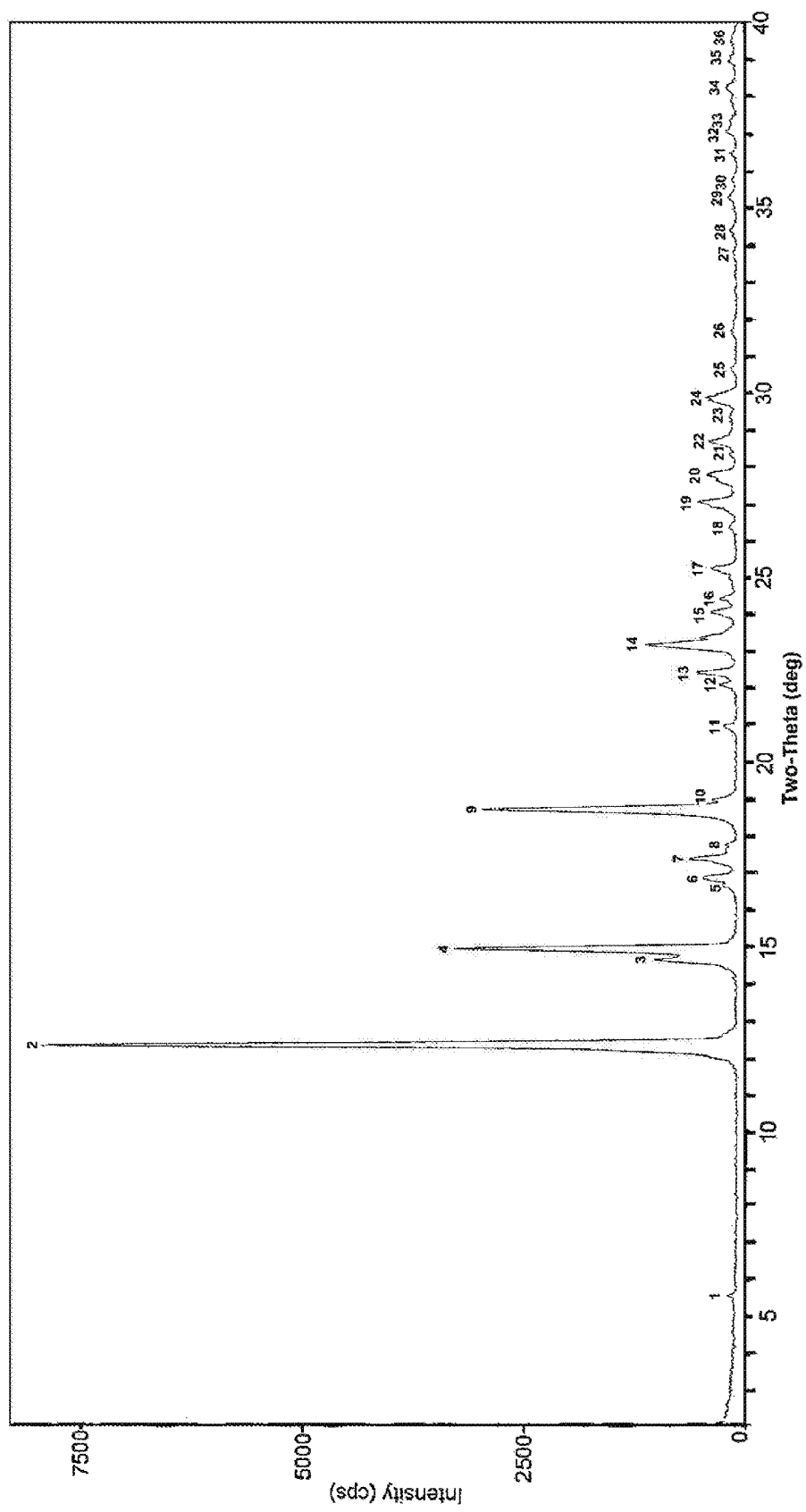

FIG. 2 discloses the x-ray diffractogram (XRD) of mesylate compound (A1).

Figure 3:
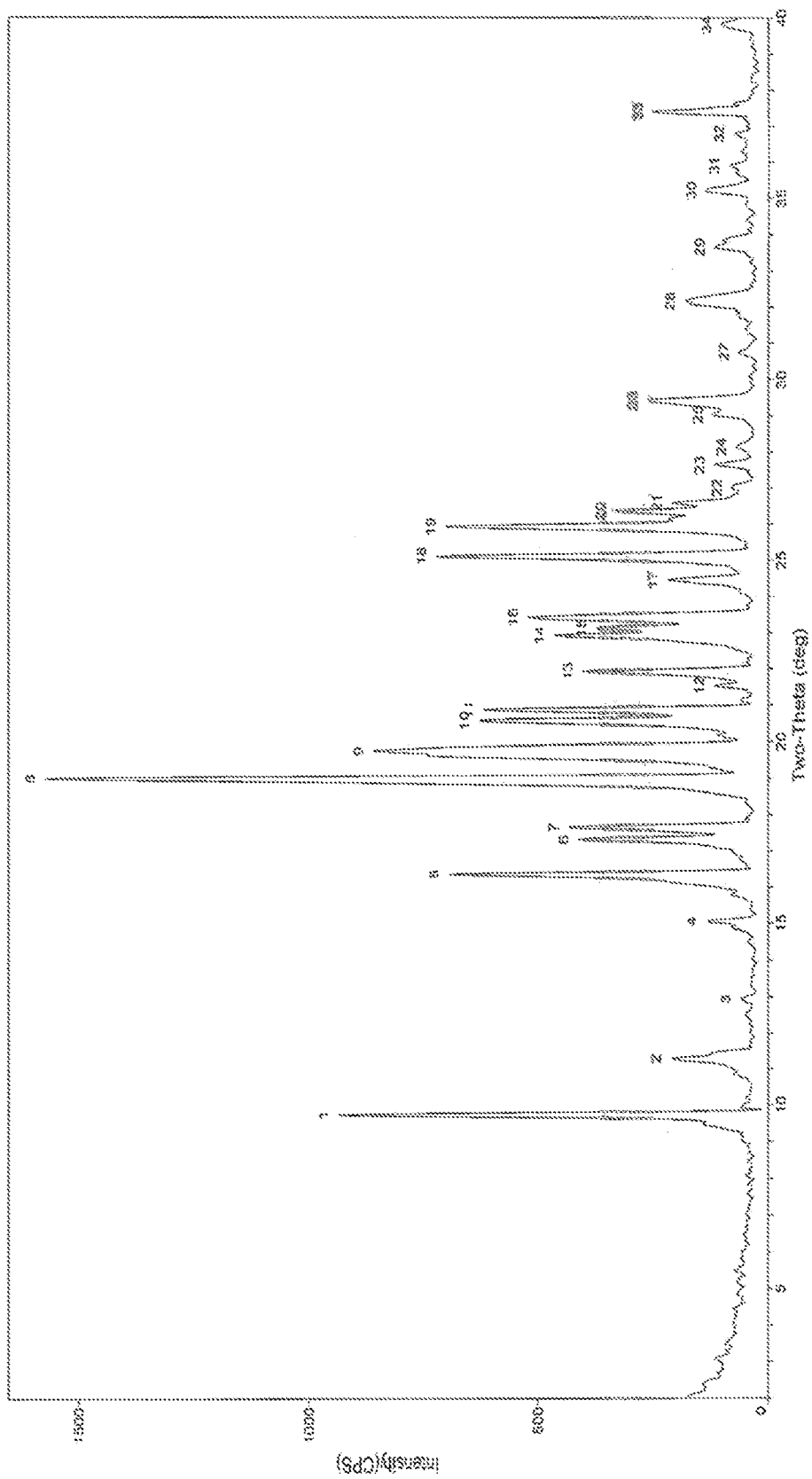

FIG. 3 discloses the x-ray diffractogram (XRD) of mesylate compound (A1) as per example-3.

DETAILED DESCRIPTION OF THE INVENTION

The above and other objects of the present invention are achieved by the process of the present invention, which leads to substantially amorphous saroglitazar magnesium suitable for pharmaceutical use and having greater stability. The invention provides an improved process for preparing substantially amorphous form of saroglitazar magnesium in a single solvent.

Optionally, the solution, prior to any solids formation, can be filtered to remove any undissolved solids, solid impurities and the like prior to removal of the solvent. Any filtration system and filtration techniques known in the art can be used.

The term "substantially amorphous" herein means amorphous form of saroglitazar having percentage crystallinity less than 25%, particularly, less than 200/%.

All ranges recited herein include the endpoints, including those that recite a range "between" two values. Terms such as "about", "generally", "substantially," and the like are to be construed as modifying a term or value such that it is not an absolute. This includes, at very least, the degree of expected experimental error, technique error and instrument error for a given technique used to measure a value.

The terms used throughout the description is defined herein below.

"DMF" refers to N,N-dimethylforamide.
"DMAc" refers to N,N-dimethylacetamide.
"DMSO" refers to N,N-dimethylsulfoxide.
"NMP" refers to N-methylpyrrolidone.
"THF" refers to tetrahydrofuran.
"MTBE" refers to methyl tert-butyl ether.
"TEA" refers to triethylamine.
"TBA" refers to tert-butyl amine.
"DIPA" refers to diisopropyl amine.

"DIPEA" refers to diisopropyl ethylamine.
"DBU" refers to 1,8-diazabicyclo[5.4.0]undec-7-ene.
"DABCO" refers to 1,4-diazabicyclo[2.2.2]octane.
"DBN" refers to 1,5-Diazabicyclo[4.3.0]non-5-ene
"HPLC" refers to high performance liquid chromatography.

In one general aspect, there is provided an improved process for the preparation of saroglitazar or its pharmaceutically acceptable salts of Formula (IB),

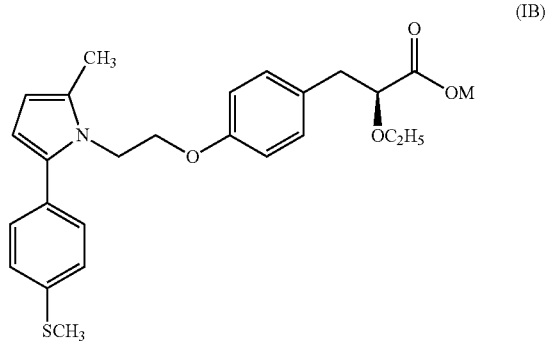
(IB)

wherein M is hydrogen or a pharmaceutically acceptable cation, the process comprising:
(a) reacting a hydroxy compound (A) with a mesylate compound (A1) to obtain alkoxy ester compound of Formula (II);

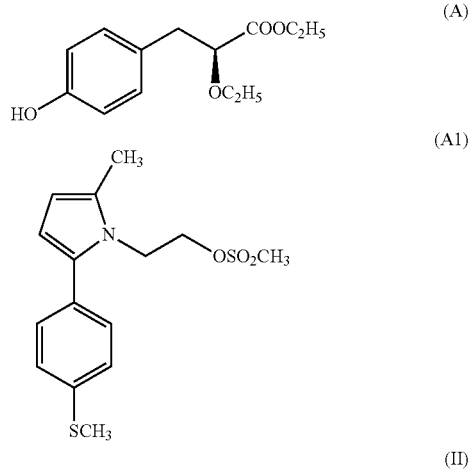
(A)
(A1)
(II)

(b) hydrolyzing the alkoxy ester compound of Formula (II) to obtain alkoxy ester compound of Formula (IB);

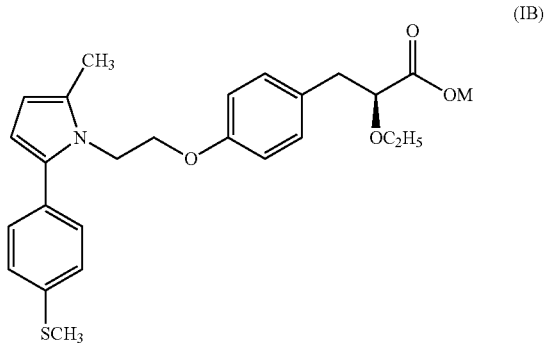
(IB)

wherein M is hydrogen or a pharmaceutically acceptable cation;
(c) optionally, neutralizing the compound of Formula (IB) wherein M is a pharmaceutically acceptable cation to obtain a compound of Formula (IB), wherein M is hydrogen; and
(d) optionally, converting the compound of Formula (IB), wherein M is hydrogen to another compound of Formula (IB), wherein M is a pharmaceutically acceptable cation.

In general, the reaction of hydroxy compound (A) with the mesylate compound (A1) is performed in one or more of organic solvents in the presence of a base and optionally in the presence of a phase transfer catalyst.

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether or mixture thereof. In particular, mixture of cyclohexane and tetrahydrofuran may be used.

The phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers like 12-crown-4, 15-crown-5, 18-crown-6, dibenzo-18-crown-6, and diaza-18-crown-6. In particular, the phase transfer catalyst may be 18-crown-6.

In general, the hydrolysis of alkoxy ester compound of Formula (II) is performed with an acid to obtain a compound of Formula (IB), wherein M is hydrogen or with a base to obtain a compound of Formula (IB), wherein M is a pharmaceutically acceptable cation.

The acid comprises of hydrochloric acid, hydrobromic acid, sulfuric acid, nitric acid, phosphoric acid, acetic acid, triflouroacetic acid, and formic acid.

In general, the reaction of the hydroxy compound (A) and the mesylate compound (A1) may be performed under heating at 35° C. to about reflux temperature of solvents. In particular, the reaction may be heated at 75° C. to 85° C. till the completion of the reaction. The reaction may be heated for 25 hours to 40 hours, preferably 36 hours.

In another general aspect, the obtained alkoxy ester (II) may be proceeded further without isolating. Therefore, the alkoxy ester (II) may be further hydrolyzed as in step (b) in-situ.

The base for hydrolyzing alkoxy ester (II) comprises of sodium hydroxide, potassium hydroxide, lithium hydroxide, calcium hydroxide, barium hydroxide, strontium hydroxide, magnesium hydroxide, zinc hydroxide, sodium carbonate, potassium carbonate, lithium carbonate, sodium bicarbonate, potassium bicarbonate, sodium hydride, potassium hydride, magnesium acetate, potassium tert-butoxide, and sodium pentoxide.

The hydrolysis of alkoxy ester of Formula (II) provides compound (IB), wherein M is a pharmaceutically acceptable cation comprises of sodium (Na), potassium (K), lithium (Li), calcium (Ca), barium (Ba), magnesium (Mg), strontium (Sr) and zinc (Zn).

In general, the pharmaceutically acceptable cation compound (IB) may optionally be neutralized to obtain the compound of Formula (IB), wherein M is hydrogen. The neutralization may be performed by addition of an acid comprising hydrochloric acid, hydrobromic acid, sulfuric acid, nitric acid, phosphoric acid, acetic acid, triflouroacetic acid, and formic acid. The pH of reaction mixture may be adjusted to 2-3 to have acidic pH.

In general, the compound of Formula (IB) wherein M is hydrogen may be further converted to compound of Formula (IB) wherein M is a pharmaceutically acceptable cation. The pharmaceutically acceptable cation comprises to alkali or alkaline earth metal cations.

The pharmaceutically acceptable cations comprises of alkali or alkaline earth metal selected from sodium, potassium, lithium, calcium, strontium, barium, magnesium and zinc.

In another general aspect, there is provided an improved process for the preparation of saroglitazar magnesium of Formula (I),

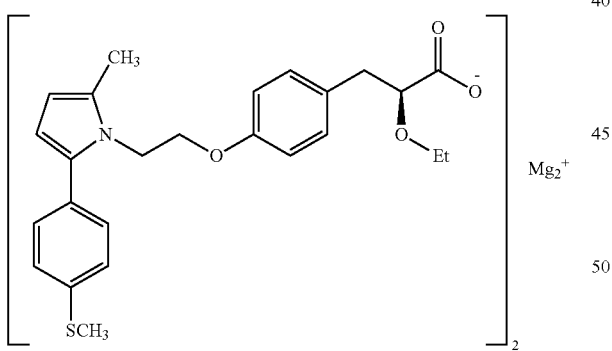

the process comprising:
(a) reacting a hydroxy compound (A) with a mesylate compound (A1) to obtain alkoxy ester compound of Formula (II);

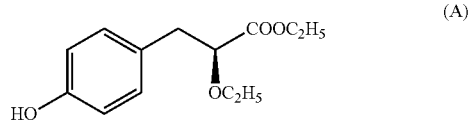

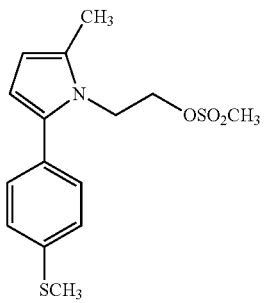

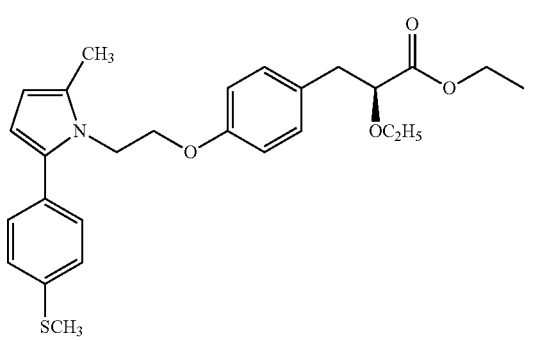

(b) hydrolyzing the alkoxy ester compound of Formula (II) to obtain a compound of Formula (IB);

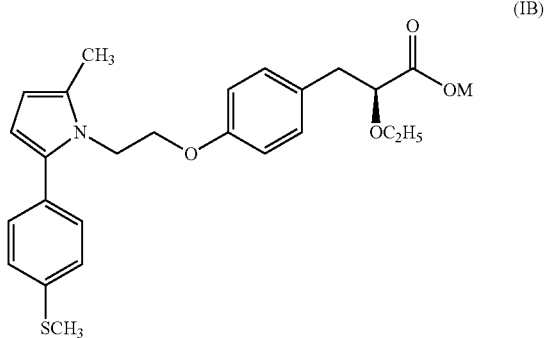

wherein M is hydrogen or a pharmaceutically acceptable cation selected from sodium (Na), potassium (K), lithium (Li), calcium (Ca), barium (Ba), strontium (Sr) and zinc (Zn);
(c) optionally, neutralizing the compound of Formula (IB) wherein M is a pharmaceutically acceptable cation to obtain a compound of Formula (IB), wherein M is hydrogen; and
(d) reacting the compound of Formula (IB), wherein M is hydrogen with a magnesium source to obtain saroglitazar magnesium of Formula (I).

In general, the compound of Formula (IB), wherein M is hydrogen or pharmaceutically acceptable cation may be prepared by the process as disclosed herein above.

The hydrolysis of alkoxy ester compound of Formula (II) is performed with an acid to obtain a compound of Formula (IB), wherein M is hydrogen or with a base to obtain a compound of Formula (IB), wherein M is a pharmaceutically acceptable cation.

In general, the pharmaceutically acceptable cation compound of Formula (IB) may optionally be neutralized to obtain a compound of Formula (IB), wherein M is hydrogen. The neutralization may be performed by addition of an acid. The acid comprising hydrochloric acid, hydrobromic acid, sulfuric acid, nitric acid, phosphoric acid, acetic acid, triflouroacetic acid, and formic acid. The pH of the reaction mixture may be adjusted to 2-3 to have an acidic pH.

In general, the base comprises of sodium hydroxide, potassium hydroxide, lithium hydroxide, calcium hydroxide, barium hydroxide, strontium hydroxide, zinc hydroxide, sodium carbonate, potassium carbonate, lithium carbonate, sodium bicarbonate, potassium bicarbonate, sodium hydride, potassium hydride, potassium tert-butoxide, and sodium pentoxide.

In general, the compound (IB) wherein M is hydrogen may be reacted with a magnesium source to obtain saroglitazar magnesium of Formula (I).

In general, the magnesium source comprises of magnesium hydroxide, magnesium methoxide, magnesium acetate, magnesium chloride, and magnesium metal. In particular, the magnesium source may be magnesium acetate tetrahydrate.

In general, the saroglitazar magnesium (I) may be obtained by the process comprising:
extracting the reaction mixture with one or more organic solvents; removing the organic solvent to obtain a residue; treating the residue with one or more organic solvents to obtain the solution; and adding the solution into an anti-solvent to obtain saroglitazar magnesium (I).

The product saroglitazar magnesium (I) thus obtained may be filtered and dried under vacuum tray drier, sieved and milled to obtain a particle size range. The milled product may be further dried till constant weight may be obtained to obtain substantially amorphous saroglitazar (I) free from residual solvents.

The organic solvent used for extraction comprises one or more of chlorinated hydrocarbons selected from methylene dichloride, ethylene dichloride, and chlorobenzene; aromatic hydrocarbons selected from toluene, xylene, and ethylbenzene.

The anti-solvent comprises one or more of aliphatic hydrocarbons selected from pentane, hexane, heptane, and cyclohexane; ethers selected from tetrahydrofuran, 1,4-dioxane, diisopropyl ether, diethyl ether, and methyl tertbutyl ether. In particular, the anti-solvent is n-heptane.

Optionally, the anti-solvent may be diluted with one or more another solvent comprising esters selected from ethyl acetate, isopropyl acetate, n-butyl acetate, t-butyl acetate, and isobutyl acetate. In particular, n-butyl acetate may be used.

The product thus obtained may be obtained by the removal of anti-solvent by the known technique in the art selected from filtration, centrifugation, decantation, a rotational distillation device such as a Buchi Rotavapor, spray drying, agitated thin film drying ("ATFD"), and freeze drying (lyophilization) or any other known techniques.

In general, the sieving of product may be done through 0.5 sieve followed by milling. Examples of such milling include various makes of ball mills, roller mills, gyratory mills, multi-mills, Jet-mills, and the like. In a preferred aspect, a mill such as a Micros Super Fine Mill (available from Nara Machinery Co. Ltd or Tokyo, Japan), Multi-Mill Sr. No. G. 1.132 (available from Grooves International Pharmaceutical & Chemical Machinery), Jet-Mill from Midas Micronizer M-100 Aerosol (No. 154/07-08 (available from microtech Engineering Company) or a common mixer grinder can be used. Alternatively another commercially available milling machine can be used.

In another general aspect, there is provided an improved process for the preparation of saroglitazar magnesium of Formula (I),

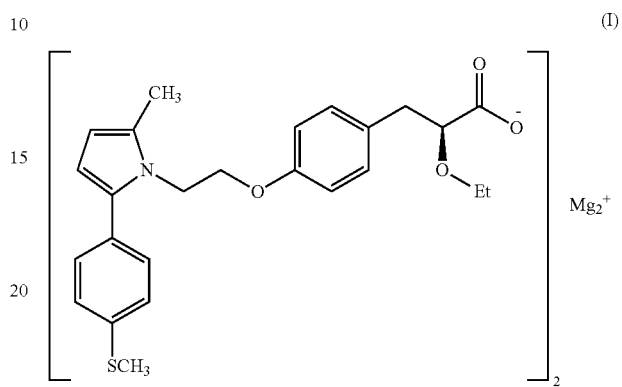

the process comprising:
(a) reacting a hydroxy compound (A) with a mesylate compound (A1) to obtain alkoxy ester compound of Formula (II);

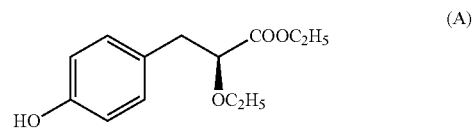

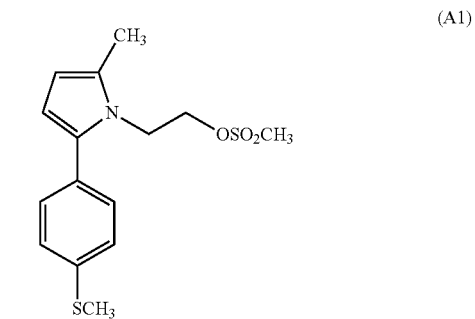

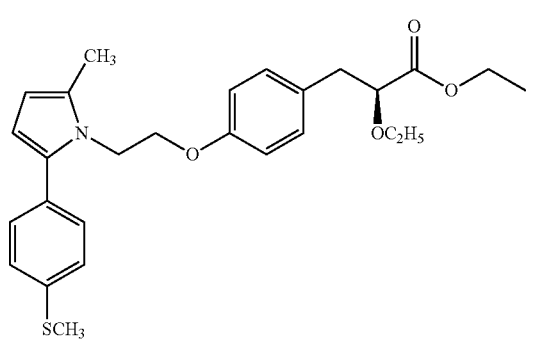

(b) hydrolyzing the alkoxy ester compound of Formula (II) with a base to obtain a compound of Formula (IB);

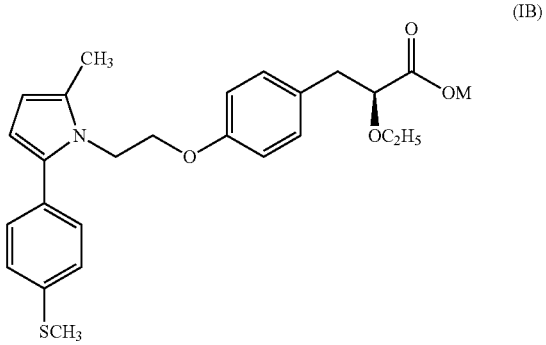

(IB)

wherein M is hydrogen or a pharmaceutically acceptable cation selected from sodium (Na), potassium (K), lithium (Li), calcium (Ca), barium (Ba), strontium (Sr) and zinc (Zn);

(c) optionally, neutralizing the compound of Formula (IB), wherein M is a pharmaceutically acceptable cation to obtain a compound of Formula (IB), wherein M is hydrogen; and (d) optionally, reacting the compound of Formula (IB), wherein M is hydrogen with an organic amine to obtain a compound of Formula (IC), and

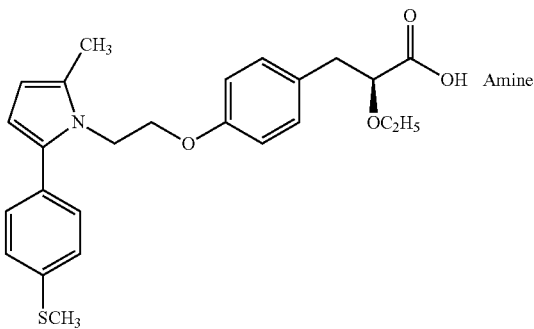

(IC)

(e) converting the compound of Formula (IC) to compound of Formula (IB), wherein M is hydrogen; and (f) reacting the compound of Formula (IB), wherein M is hydrogen with a magnesium source to obtain saroglitazar magnesium of Formula (I).

In general, the compound of Formula (IB), wherein M is hydrogen or pharmaceutically acceptable cation may be prepared by the process as disclosed herein above.

The hydrolysis of alkoxy ester compound of Formula (II) is performed with an acid to obtain a compound of Formula (IB), wherein M is hydrogen or with a base to obtain a compound of Formula (IB), wherein M is a pharmaceutically acceptable cation.

In general, the pharmaceutically acceptable cation compound of Formula (IB) may optionally be neutralized to obtain a compound of Formula (IB), wherein M is hydrogen. The neutralization may be performed by addition of an acid comprising hydrochloric acid, hydrobromic acid, sulfuric acid, nitric acid, phosphoric acid, acetic acid, triflouroacetic acid, and formic acid. The pH of the reaction mixture may be adjusted to 2-3 to have an acidic pH.

In general, the base comprises of sodium hydroxide, potassium hydroxide, lithium hydroxide, calcium hydroxide, barium hydroxide, strontium hydroxide, zinc hydroxide, sodium carbonate, potassium carbonate, lithium carbonate, sodium bicarbonate, potassium bicarbonate, sodium hydride, potassium hydride, potassium tert-butoxide, and sodium pentoxide.

The compound of Formula (IB), wherein M is hydrogen may be further reacted with organic amine to obtain the compound of Formula (IC). The organic amine comprises of ammonia, methylamine, dimethylamine, ethylamine, diethylamine, 1,2-ethanediamine, n-propylamine, isopropylamine, diisopropylamine, N-methyl isopropylamine, n-butylamine, t-butylamine, 2-butamine, 1,2-ethanediamine, N-methylglucamine, N,N,N-trimethylethanolamine hydroxide (choline), tromethamine, cyclohexylamine, N-methylcyclohexylamine, guanidine, N-(4-aminobutyl)-guanidine dicyclohexylamine, benzenemethanamine, ethanolamine, diethanolamine, tris(hydroxymethyl)methylamine, hydroxylamine, methanaminium, benzylamine, N-methylbenzylamine, N-ethylbenzylamine, (R,S)-1-phenylethylamine, (S)-1-phenylethylamine, (R)-1-phenylethylamine, 4-methoxybenzylamine, pyrrolidine, piperidine, piperazine, morpholine, 2-aminopyrimidine, L-alanine, L-lysine, D-lysine, L-arginine, L-histidine, L-threonine, 2-thiopheneethanamine, (2S)-3,3-dimethyl-2-butanamine, cyclopentanamine, and cycloheptanamine. In particular, (S)-1-phenyl ethylamine may be prepared.

In general, the compound (IC) may optionally be neutralized to obtain a compound of Formula (IB), wherein M is hydrogen. The neutralization may be performed by addition of an acid comprising hydrochloric acid, hydrobromic acid, sulfuric acid, nitric acid, phosphoric acid, acetic acid, triflouroacetic acid and formic acid. The pH of reaction mixture may be adjusted to 2-3 to have acidic pH.

In general, the compound (IB) wherein M is hydrogen may be reacted with a magnesium source to obtain saroglitazar magnesium of Formula (I).

In general, the magnesium source comprises magnesium hydroxide, magnesium methoxide, magnesium acetate, magnesium chloride and magnesium metal. In particular, the magnesium source may be magnesium acetate tetrahydrate.

In general, the saroglitazar magnesium (I) may be obtained by extracting the reaction mixture with one or more of organic solvent followed by washing the organic layer and removal of the organic solvent to obtain a residue. The residue may be treated with same solvent and added into an anti-solvent to obtain saroglitazar magnesium (I). The product thus obtained may be, filtered and dried under vacuum tray drier, sieved and milled to obtained suitable particle size range. The milled product may be further dried till constant weight may be obtained to obtain substantially amorphous saroglitazar (I) free from residual solvents.

The organic solvent used for extraction comprises one or more of chlorinated hydrocarbons selected from methylene dichloride, ethylene dichloride and chlorobenzene; aromatic hydrocarbons selected from toluene, xylene, and ethylbenzene.

The anti-solvent comprises one or more of aliphatic hydrocarbons selected from pentane, hexane, heptane and cyclohexane; ethers selected from tetrahydrofuran, 1,4-dioxane, diisopropyl ether, diethyl ether, and methyl tertbutyl ether. In particular, the anti-solvent may be n-heptane.

Optionally, the anti-solvent may be diluted with one or more of another solvent comprises of esters selected from ethyl acetate, isopropyl acetate, n-butyl acetate, t-butyl acetate and isobutyl acetate. In particular, n-butyl acetate may be used.

In another general aspect, there is provided a process for the preparation of saroglitazar magnesium of Formula (I),

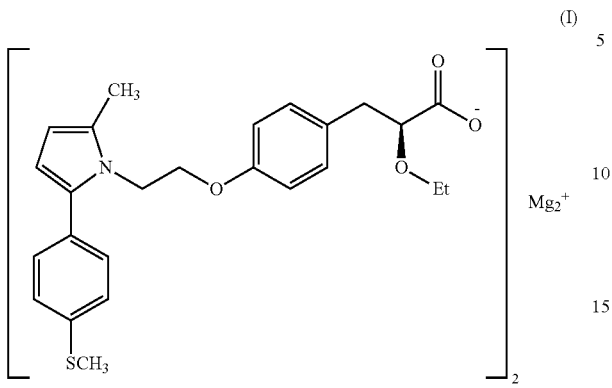

the process comprising:
(a) reacting 2-bromo-1-(4-(methylthio)phenyl)ethanone (E1) with methyl acetoacetate in one or more of organic solvents in the presence of a base to obtain a compound (D1);

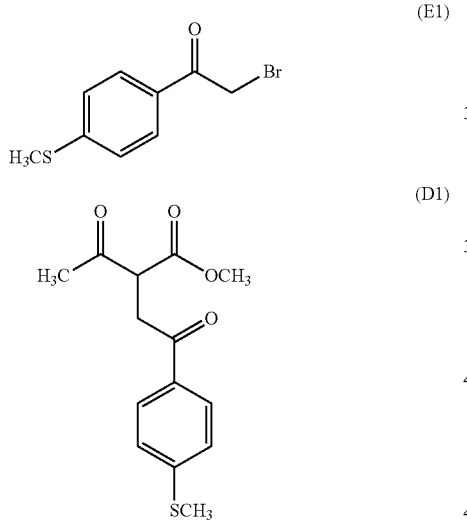

(b) hydrolyzing the compound (D1) in-situ with a base followed by decarboxylation to obtain the compound (C1);

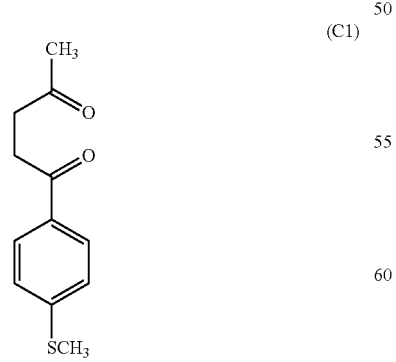

(c) reacting the compound (C1) in-situ with ethanolamine under Paal-Knoor conditions in the presence of an acid to obtain the compound (B1);

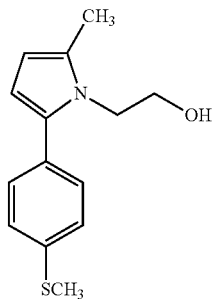

(d) reacting the compound (B1) in-situ with methane sulphonyl chloride in the presence of a base to obtain mesylate compound (A1);

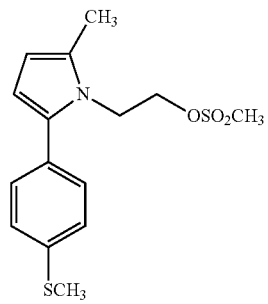

(e) reacting the mesylate compound (A1) in-situ with a hydroxy compound (A) with in the presence of base to obtain an alkoxy ester compound of Formula (II);

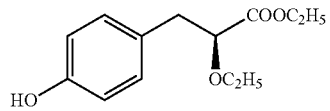

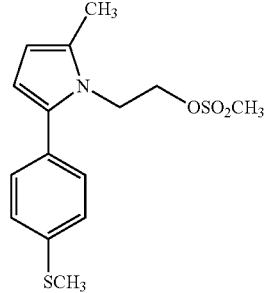

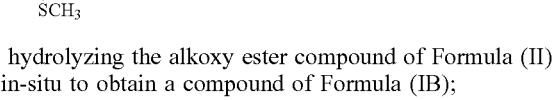

(f) hydrolyzing the alkoxy ester compound of Formula (II) in-situ to obtain a compound of Formula (IB);

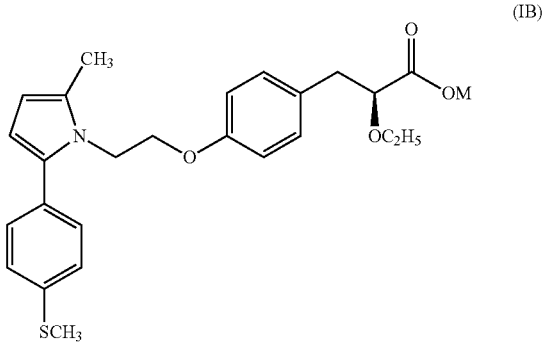

(IB)

wherein M is hydrogen or a pharmaceutically acceptable cation selected from sodium (Na), potassium (K), lithium (Li), calcium (Ca), barium (Ba), strontium (Sr) and zinc (Zn);

(g) optionally, neutralizing the compound of Formula (IB) wherein M is a pharmaceutically acceptable cation to obtain the compound of Formula (IB), wherein M is hydrogen; and (h) reacting the compound of Formula (IB), wherein M is hydrogen with a magnesium source to obtain saroglitazar magnesium of Formula (I), wherein the process does not involve isolation of intermediates.

In general, the organic solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbon tetrachloride. In particular, toluene, xylene, methylene dichloride, and ethyl acetate may be used.

The base in step (a) comprises one or more of alkali or alkaline earth metals hydroxide, carbonates, bicarbonates, hydrides, alkoxides etc. In particular, sodium hydroxide, potassium hydroxide, lithium hydroxide, calcium hydroxide, sodium carbonate, potassium carbonate, sodium bicarbonate, potassium bicarbonate, sodium hydride, potassium hydride, sodium methoxide, potassium tert-butoxide, and sodium pentoxide. More particularly, sodium methoxide may be used.

The embodiments of the process may further comprise of in-situ hydrolyzing the compound (D1) without isolating from step (a) as the scope of the invention.

The compound (D1) may be hydrolyzed with same or different bases. The base for hydrolysis comprises one or more of alkali or alkaline earth metals hydroxide, carbonates, bicarbonates, hydrides, alkoxides etc. In particular, sodium hydroxide, potassium hydroxide, lithium hydroxide, calcium hydroxide, sodium carbonate, potassium carbonate, sodium bicarbonate, potassium bicarbonate, sodium hydroxide, potassium hydride, sodium methoxide, potassium tert-butoxide, and sodium pentoxide. More particularly, sodium hydroxide may be used.

The reaction mixture may be preferably diluted with one or more of another solvent. The another solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate. In particular, methanol may be used.

The compound (C1) may be obtained by decarboxylation of carboxylic acid derivative obtained in-situ which may be not isolated.

It general, the compound (B1) may be obtained by treating the diketo compound (C1) with ethanolamine under Paal-Knorr conditions in presence of an acid. The acid comprising acetic acid, hydrochloric acid, sulfuric acid, formic acid, hydrobromic acid, trifluoroacetic acid, and pivalic acid. In particular, the pivalic acid may be used.

The compound (B1) may be in-situ proceed for further reaction. The solvent system may be same. In particular, the solvent for further reaction may be toluene.

The compound (B1) obtained in step (c) may be reacted with methane sulphonyl chloride in toluene in the presence of a base to obtain mesylate compound (A1).

The base for step (d) comprises one or more of alkali metal hydroxides selected from sodium hydroxide, potassium hydroxide, and lithium hydroxide; alkali metal carbonates selected from sodium carbonate, potassium carbonate, and cesium carbonate; alkali metal bicarbonates selected from sodium bicarbonate, and potassium bicarbonate; ammonia or its aqueous solution; organic bases selected from methyl amine, ethyl amine, TEA, TBA, DIPA, DIPEA, pyridine, piperidine, morpholine, DBU, DABCO and DBN. In particular, TEA may be used.

In general, the mesylate compound (A1) may be in-situ reacted with the hydroxy compound (A) in the presence of a base and optionally in the presence of a phase transfer catalyst.

The base comprises of alkali or alkaline earth metals hydroxide, carbonates, bicarbonates, hydrides, alkoxides etc. In particular, sodium hydroxide, potassium hydroxide, lithium hydroxide, calcium hydroxide, sodium carbonate, potassium carbonate, sodium bicarbonate, potassium bicarbonate, sodium hydroxide, potassium hydride, potassium tert-butoxide, sodium pentoxide and the like. More particularly, potassium carbonate may be used.

The phase transfer catalyst comprises of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers like 12-crown-4, 15-crown-5, 18-crown-6, dibenzo-18-crown-6, diaza-18-crown-6 and the like. In particular, the phase transfer catalyst may be 18-crown-6.

In general, the reaction of hydroxy compound (A) and mesylate compound (A1) may be performed under heating at 35° C. to about reflux temperature of solvents. In particular, the reaction may be heated at 75° C. to 85° C. till the completion of the reaction. The reaction may be heated for 25 hours to 40 hours, preferably 36 hours.

The hydrolysis of alkoxy ester compound of Formula (II) obtained is performed with an acid to obtain a compound of Formula (IB) wherein M is hydrogen or with a base to obtain a compound of Formula (IB) wherein M is a pharmaceutically acceptable cation.

The acid comprising hydrochloric acid, hydrobromic acid, sulfuric acid, nitric acid, phosphoric acid, acetic acid, triflouroacetic acid, and formic acid.

The base for hydrolyzing alkoxy ester (II) comprises of alkali or alkaline earth metals hydroxide, carbonates, bicarbonates, hydrides etc. In particular, sodium hydroxide, potassium hydroxide, lithium hydroxide, calcium hydroxide, sodium carbonate, potassium carbonate, sodium bicarbonate, potassium bicarbonate, sodium hydroxide, and potassium hydride. In particular, sodium hydroxide may be used.

In general, the compound (IB) wherein M is hydrogen may be reacted with a magnesium source to obtain saroglitazar magnesium of Formula (I).

In general, the magnesium source comprises magnesium hydroxide, magnesium methoxide, magnesium acetate, magnesium chloride, and magnesium metal. In particular, the magnesium source may be magnesium acetate tetrahydrate.

In general, the saroglitazar magnesium (I) may be obtained by extracting the reaction mixture with one or more of organic solvent followed by washing the organic layer and removal of the organic solvent. The residue may be treated with the same solvent and added into an anti-solvent to obtain the saroglitazar magnesium (I).

The product thus obtained may be filtered and dried under vacuum tray drier, sieved and milled to obtained suitable particle size range. The milled product may be further dried till constant weight may be obtained to obtain substantially amorphous saroglitazar (I) free from residual solvents.

In general, the organic solvent comprises one or more of toluene, xylene, ethyl acetate and methylene dichloride. The saroglitazar magnesium of Formula (I) may be obtained by removal of solvent and treatment with an anti-solvent.

The anti-solvent comprises one or more of aliphatic hydrocarbons selected from pentane, hexane, heptane, and cyclohexane; ethers selected from tetrahydrofuran, 1,4-dioxane, diisopropyl ether, diethyl ether; and methyl tertbutyl ether. In particular, the anti-solvent may be n-heptane.

Optionally, the anti-solvent may be diluted with one or more of another solvent comprising esters selected from ethyl acetate, isopropyl acetate, n-butyl acetate, t-butyl acetate, and isobutyl acetate. In particular, n-butyl acetate may be used.

In another general aspect, there is provided an improved process for the preparation of mesylate compound of Formula (A1),

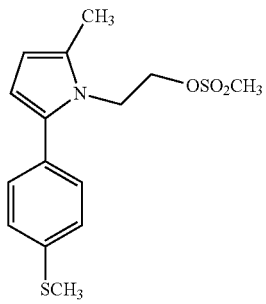
(A1)

the process comprising:
(a) reacting 4-(methylthio)benzaldehyde and methylvinylketone in the presence of a base and a stetter catalyst to obtain compound (C1);

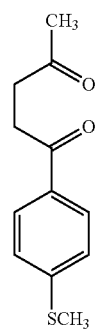
(C1)

(b) reacting the compound (C1) with ethanolamine under Paal-Knoor conditions in the presence of an acid to obtain compound (B1);

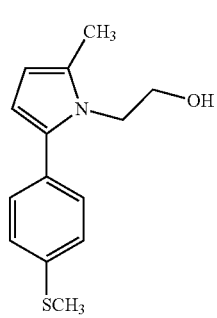
(B1)

(c) reacting the compound (B1) with methane sulphonyl chloride in the presence of a base in one or more of organic solvents to obtain the mesylate compound (A1); and
(d) optionally, purifying the mesylate compound of Formula (A1).

In general, the reaction of 4-(methylthio)benzaldehyde and methylvinylketone is performed in the presence of a stetter catalyst. The stetter catalyst comprises of alkylthiazolium halide of Formula (C),

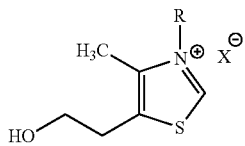
(C)

wherein R=$C_1$-$C_{12}$ alkyl like methyl, ethyl, propyl, butyl, and dodecyl; and
X=halide like chloride, fluoride, bromide, and iodide.

In particular, the stetter catalyst is 5-(2-hydroxyethyl)-3,4-dimethylthiazol-3-ium iodide (C-stetter).

In general, the reaction may be performed in the presence or absence of organic solvent. When the reaction is performed in presence of organic solvent, the organic solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbontetrachloride.

The base in step (a) comprises one or more of alkali metal hydroxides selected from sodium hydroxide, potassium hydroxide, lithium hydroxide; alkali metal carbonates selected from sodium carbonate and potassium carbonate; alkali metal bicarbonates selected from sodium bicarbonate and potassium bicarbonate; ammonia or its aqueous solution; organic bases selected from methyl amine, ethyl amine, TEA, TBA, DIPA, DIPEA, pyridine, piperidine, morpholine, DBU, DABCO and DBN. In particular, TEA may be used.

In general, the compound (B1) may be obtained by treating the diketo compound (C1) with ethanolamine under Paal-Knoor conditions in presence of an acid. The acid comprises of acetic acid, hydrochloric acid, sulfuric acid, formic acid, hydrobromic acid, trifluoroacetic acid, and pivalic acid. In particular, the pivalic acid may be used.

The compound (B1) may be in-situ proceed for further reaction. The solvent system may be same. In particular, the suitable solvent for further reaction may be toluene. The compound (B1) obtained in step (b) may be reacted with methane sulphonyl chloride in toluene in the presence of base to obtain mesylate compound (A1).

The base for step (c) comprises one or more of alkali metal hydroxides selected from sodium hydroxide, potassium hydroxide, lithium hydroxide; alkali metal carbonates selected from sodium carbonate and potassium carbonate' alkali metal bicarbonates selected from sodium bicarbonate and potassium bicarbonate; ammonia or its aqueous solution; organic bases selected from methyl amine, ethyl amine, TEA, TBA, DIPA, DIPEA, pyridine, piperidine, morpholine, DBU, DABCO and DBN. In particular, TEA may be used.

The compound (A1) may be isolated by removal of toluene by distillation followed by treating the residue with methanol and removal of methanol to obtain wet-cake. The wet product may be dried in vacuum tray dryer to obtain constant weight.

The compound (A1) obtained may be characterized by x-ray powder diffraction as crystalline. The crystalline mesylate compound (A1) is crystalline Form-I characterized by x-ray powder diffraction having characteristic peaks at about 12.4, 15.0, 17.7 and 23.2±0.2° 2θ and x-ray powder diffraction pattern substantially as shown as in FIG. 2.

The compound (A1) may be optionally purified in one or more of organic solvent. The organic solvent comprises of esters selected from ethyl acetate, isopropyl acetate, n-butyl acetate, t-butyl acetate, and isobutyl acetate; alcohols selected from methanol, ethanol, isopropanol, n-butanol, and t-butanol; ketones selected from acetone, methyl isobutyl ketone, and methyl ethyl ketone, or mixtures thereof. In particular, the mixture of ethyl acetate and methanol may be used.

The crystalline mesylate compound (A1) obtained by purification is crystalline Form-II characterized by x-ray powder diffraction having characteristic peaks at about 9.7, 16.4, 17.3, 17.7, 19.0, 19.7, 20.6, 20.9, 21.9, 25.1, 25.9 and 29.4±0.2° 2θ and x-ray powder diffraction pattern substantially as shown as in FIG. 3.

In general aspect, there is provided use of crystalline mesylate compound (A1) for the preparation of substantially amorphous saroglitazar magnesium.

In another general aspect, there is provided substantially amorphous saroglitazar magnesium substantially free from residual solvents.

In another general aspect, the substantially amorphous saroglitazar magnesium is characterized by X-ray powder diffraction pattern substantially as depicted in FIG. 1.

Powder X-ray Diffraction of saroglitazar magnesium and mesylate compound (A1) can be obtained under following conditions.

Powder X-Ray Diffraction: X-ray powder diffraction spectrum was observed on a MF 2100 2 KW X-ray Powder diffractometer of make Rigaku having a Copper Kα-radiation at a voltage of 40 kV and 30 mA. Approximately 150 mg sample was gently flattened on a quartz plate without further processing (e.g. Grinding and 0.5 sieving) and scanned from 4° to 40° at 0.010° sampling width and 4.000° per minute.

In another general aspect, saroglitazar magnesium along with its intermediates may be prepared by the reaction scheme-1, scheme-2 and scheme-3 as shown below, which is also the scope of the present invention.

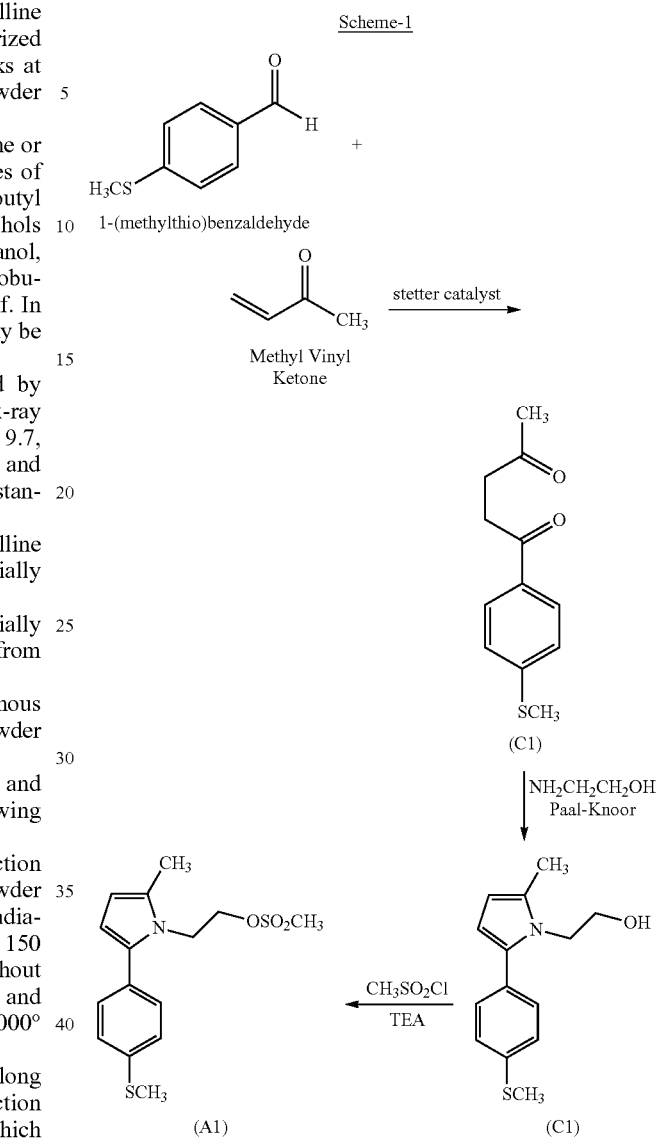

Scheme-1

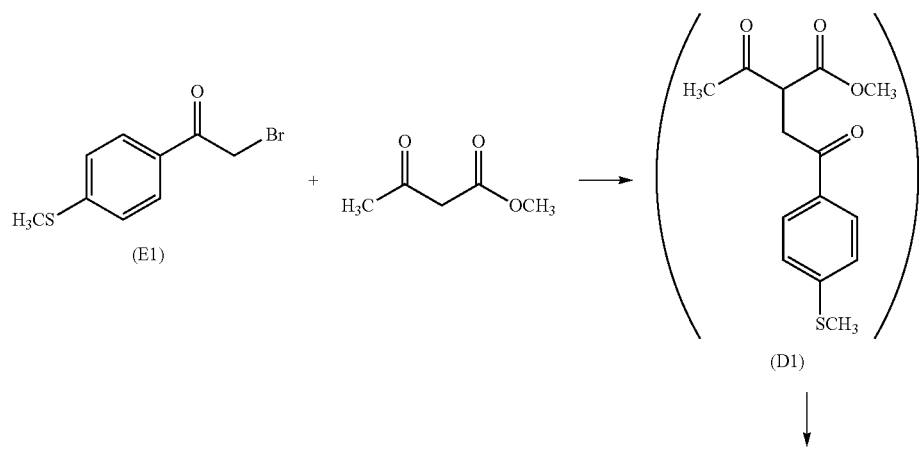

Scheme-2

-continued
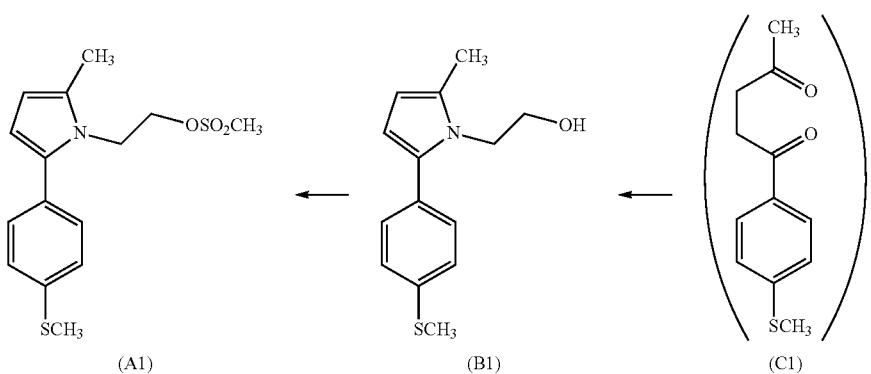
Scheme-3
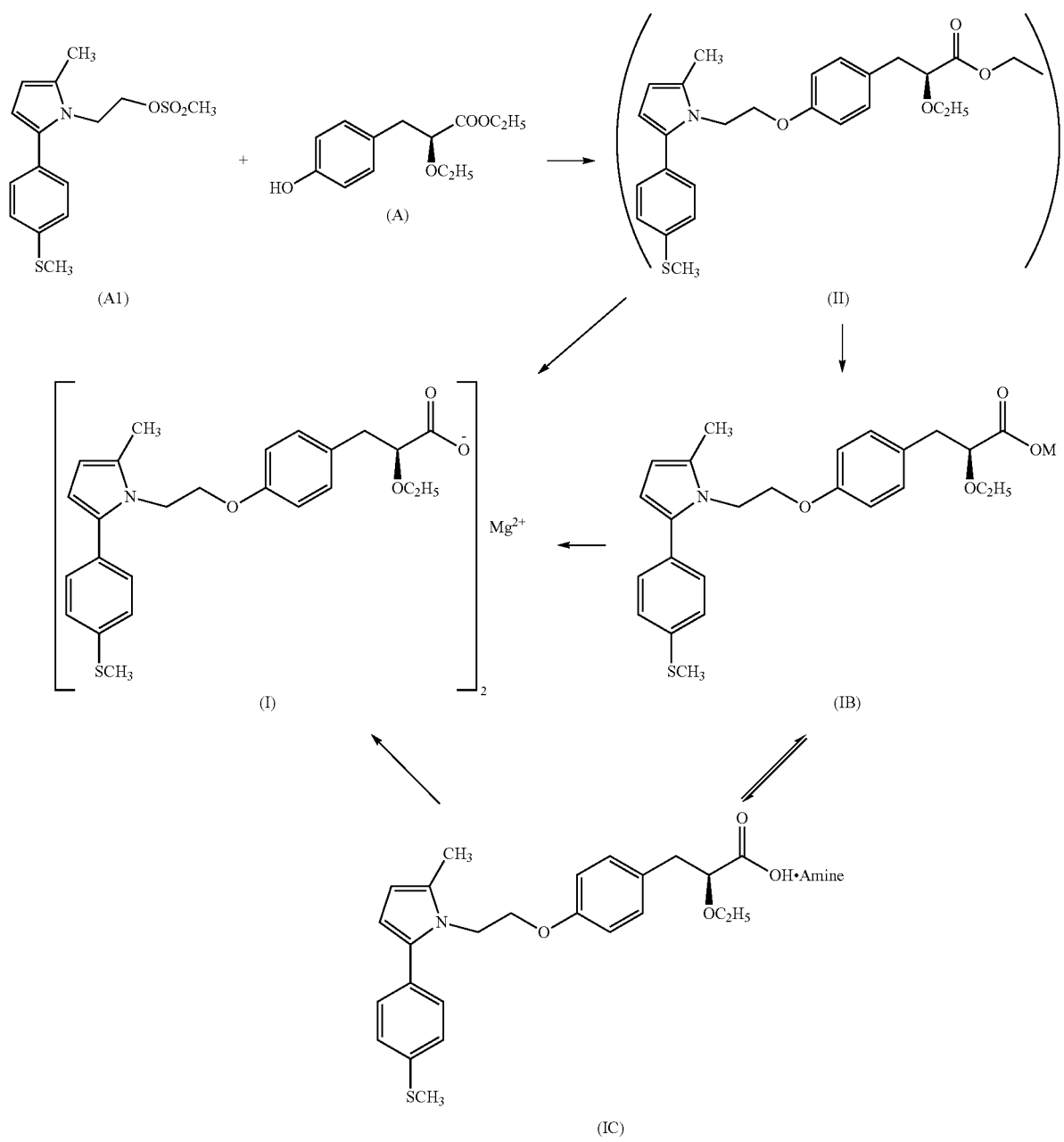

The invention also encompasses pharmaceutical compositions comprising saroglitazar of the invention. As used herein, the term "pharmaceutical compositions" includes pharmaceutical formulations like tablets, pills, powders, liquids, suspensions, emulsions, granules, capsules, suppositories, or injection preparations.

In another general aspect, there is provided a pharmaceutical composition comprising substantially amorphous saroglitazar magnesium prepared by the process of the present invention together with one or more of pharmaceutically acceptable carriers, excipients or diluents.

The present invention is further illustrated by the following example which is provided merely to be exemplary of the invention and do not limit the scope of the invention.

EXAMPLES

Example-1

Preparation of methanesulfonic acid 2-[2-methyl-5-(4-methylsulfanyl-phenyl)-pyrrol-1-yl]-ethyl ester (A1)

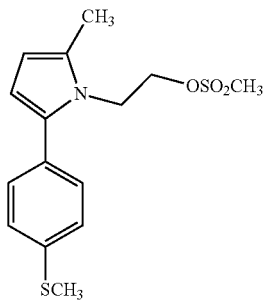

In a 5 Liter three necked round bottom flask equipped with nitrogen atmosphere facility, mechanical stirrer, thermometer and an addition funnel, sodium methoxide (165 g) and toluene (1000.0 ml) were added under nitrogen environment and cooled to 8° C. to 12° C. Methyl acetoacetate (331.55 g) was added dropwise and stirred for 1 hour. 2-bromo-1-(4-methyl sulfonyl phenyl) ethanone (500.0 g) compound (E1) in toluene (1500.0 ml) and sodium sulfate (75.0 g) mixture was stirred for 10 min and filtered at 25° to 35° C. The filtrate as obtained was added dropwise into the previous reaction mixture and stirred at 30° C. to 35° C. for 30 min. The organic layer was collected and washed with 10% sodium bicarbonate solution. The separated organic layer was collected and washed with water. 2-[2-(4-Methyl sulfanyl-phenyl)-2-oxo-ethyl]-3-oxo-butynic acid methyl ester as obtained in toluene layer is diluted with methanol (2500 ml) and sodium hydroxide solution (89.75 g) in water (2500 ml) was added and heated to 50° to 55° C. for 1 hour. The layers were separated and the toluene layer was collected and heated to 45° to 55° C. and charcoalized. The reaction mixture was filtered and pivalic acid (57.3 g) and ethanol amine (143.9 g) were added and heated to 105° to 115° C. for removing water azeotropically. The toluene layer was separated and triethyl amine (271.85 g) was added at 25° to 35° C. and the reaction mixture was cooled to 10° to 20° C. Methane sulphonyl chloride (282.5 g) was added dropwise, and stirred for 2 hours and heated to 35° to 45° C. The reaction mixture was filtered and washed with toluene. Toluene was distilled out completely under the vacuum to obtain the residue. The residue was dissolved in toluene (1500 mL) and used for further process.

Example-2

Preparation of methanesulfonic acid 2-[2-methyl-5-(4-methylsulfanyl-phenyl)-pyrrol-1-yl]-ethyl ester (A1)

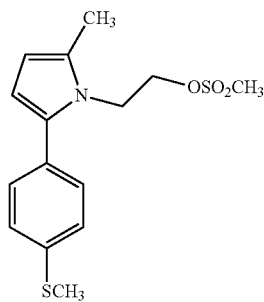

In a 250 mL three necked round bottom flask equipped with nitrogen atmosphere facility, mechanical stirrer, thermometer and an addition funnel, 4-(methylthio)benzaldehyde (10 g), methyl vinyl ketone (3.63 g), triethylamine (9.95 g) and 3-methyl-5-(2-hydroxyethyl)-4-methyl thiazolium iodide (stetter catalyst) (2.8 g) were heated to 70° C. to 80° C. and maintained overnight. The reaction mixture was cooled to room temperature and ethanol (100 mL) was added. The reaction mixture was stirred for 30 min and filtered. The product was washed with ethanol and dried to obtain 1,4-diketo compound (C1).

1,4-diketo compound (C1) obtained above and toluene (50 mL) were heated to 45° to 55° C. and charcoalized. The reaction mixture was filtered and pivalic acid (5.7 g) and ethanol amine (14.4 g) were added and heated to 105° to 115° C. and cooled to 25° C. Triethyl amine (27.2 g) was added at 25° to 35° C. and the reaction mixture was cooled to 10° to 20° C. Methane sulphonyl chloride (28.3 g) was added dropwise, and stirred for 2 hours and heated to 35° to 45° C. The reaction mixture was filtered and washed with toluene. Toluene was distilled out completely under the vacuum, methanol (2500 ml) was added and heated to 55° to 65° C. and charcoalized for 30 min. The reaction mixture was filtered and washed with methanol. The reaction mixture was cooled to 25° to 35° C. and stirred for 30 min. Reaction mass was further cooled to −5° to 5° C. and filtered. The wet-cake was washed with methanol and dried to obtain compound (A1). The compound (A1) was characterized as crystalline solid by x-ray powder diffraction (FIG. 2).

Example-3

Purification of methanesulfonic acid 2-[2-methyl-5-(4-methylsulfanyl-phenyl)-pyrrol-1-yl]-ethyl ester (A1)

In a 250 mL three necked round bottom flask equipped with nitrogen atmosphere facility, mechanical stirrer, thermometer and an addition funnel, 70 g methanesulfonic acid 2-[2-methyl-5-(4-methylsulfanyl-phenyl)-pyrrol-1-yl]-ethyl ester (A1) and 420 mL ethyl acetate were added at 25° C. The reaction mixture was stirred for 30 min to obtain clear solution. 3.5 g charcoal was added and stirred for 30 min. The reaction mixture was filtered and washed with ethyl acetate. The filtrate was concentrated and 315 mL methanol was added. The reaction mixture was stirred for 2 hours at 25° C. and cooled to 0° C. The product precipitated was filtered and washed with methanol to obtain crystalline compound (A1). The compound (A1) was characterized as crystalline solid by x-ray powder diffraction (FIG. 3).

Example-4

Preparation of Saroglitazar Magnesium (I)

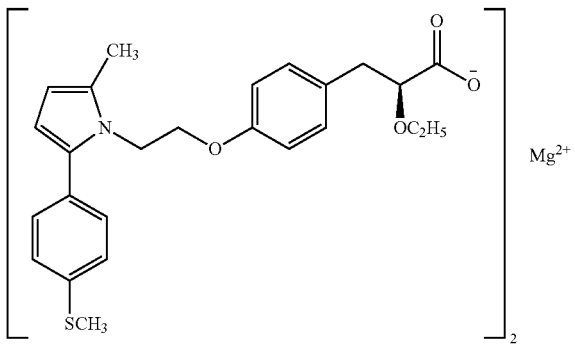

In a 5 Liter three necked round bottom flask equipped with nitrogen atmosphere facility, mechanical stirrer, thermometer and an addition funnel, 2-ethoxy-3-(4-hydroxy-phenyl)-propionic acid ethyl ester (A) (100.0 g) and toluene (1300.0 ml) were charged and reaction mixture was heated to 45° to 55° C. Potassium carbonate (58.0 g) was added and stirred for 30 min. Toluene solution of methanesulfonic acid 2-[2-methyl-5-(4-methylsulfanyl-phenyl)-pyrrol-1-yl]-ethyl ester (A1) (150.24 g) obtained in example-1, 18-Crown-6 (5.0 g) and THF (200.0 ml) were added and heated to 75° C. to 85° C. for 36 hour. The reaction mixture was cooled to 25° to 35° C. and water (1000.0 ml) was added and stirred for 15 min. The separated aqueous layer was treated with toluene (200.0 ml) and stirred for 15 min. The organic layers were combined and washed with caustic solution (600.0 ml). The separated organic layer was washed with water (600.0 ml) and characoalized with HP-120 (5.0 g) charcoal and stirred for 30 min and filtered. The filtrate was added sodium hydroxide 20.14 g solution in water (200.0 ml) and the reaction mixture was stirred for 3 hours. The reaction mixture was diluted with water (1800.0 ml) and stirred for 15 min. The separated aqueous layer was washed with n-butyl acetate. The separated aqueous layer was added magnesium acetate tetrahydrate solution (90.0 g) in water (100.0 ml) and stirred for 1 hour. The aqueous layer was extracted with methylene dichloride (2000 ml). The separated organic layer was washed with sodium chloride solution and charcoalized. The charcoalized solution was filtered and filtrate was distilled to remove toluene completely. The residue was diluted with toluene (1000 ml) and stirred for 30 min. The organic solution was added into n-heptane (1500 mL) and stirred for 3 hours. The product was filtered and washed with n-heptane and dried in vacuum tray dryer at 25° C. to 30° C. for 3 hours. The product was sieved through 0.5 mm sieve and milled through jet-milled. The product was further dried in vacuum tray drier at 40° C. to 50° C. for 6 hours followed by drying at 55° C. to 65° C. for 40 hours to obtain amorphous saroglitazar magnesium (I). The compound is characterized by x-ray power diffraction (FIG. 1).

The reaction of methanesulfonic acid 2-[2-methyl-5-(4-methylsulfanyl-phenyl)-pyrrol-1-yl]-ethyl ester (A1) and 2-ethoxy-3-(4-hydroxy-phenyl)-propionic acid ethyl ester (A) may also be performed in similar manner as above in absence of phase transfer catalyst 18-Crown-6.

Example-5

Preparation of saroglitazar (S)-(–)-phenyl ethylamine salt

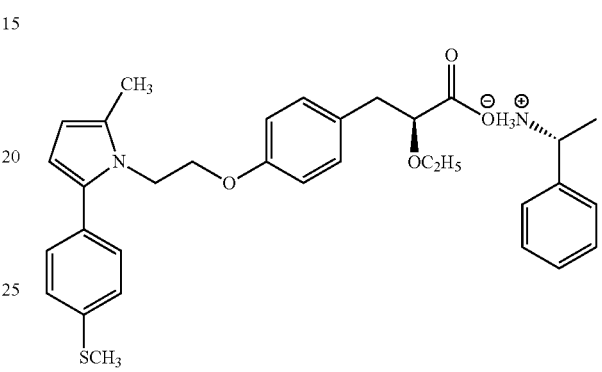

In a 250 mL three necked round bottom flask equipped with nitrogen atmosphere facility, mechanical stirrer, thermometer and an addition funnel, residue-A obtained in example-1 and ethanol (400 mL) were stirred for 15 min. Sodium hydroxide 20.14 g solution in water (200.0 ml) was added and the reaction mixture was stirred for 3 hours. The reaction mixture was diluted with water (1800.0 ml) and stirred for 15 min. The separated aqueous layer was washed with isopropyl acetate (400 mL). The separated aqueous layer was diluted with isopropyl acetate (500 mL) and acidified with conc. HCl at adjust the pH 2-3. The separated aqueous layer was washed with isopropyl acetate. The combined organic layer was treated with (S)-(–)-phenyl ethylamine (55.94 g) and stirred for 2 hours at 25° C. and 30 min at 45° C. The reaction mixture was cooled to 0° C. and stirred for 2 hours, filtered and washed with isopropyl acetate. The wet-cake was dried to obtain saroglitazar phenyl ethylamine salt.

Example-6

Preparation of saroglitazar magnesium from saroglitazar (S)-(–)-phenyl ethylamine salt In a 250 mL three necked round bottom flask equipped with nitrogen atmosphere facility, mechanical stirrer, thermometer and an addition funnel, saroglitazar phenyl ethylamine wet-cake obtained in example-7 and isopropyl acetate (800 mL) were added at 25° C. The reaction mixture was diluted with water (400.0 ml) and acidified with conc. HCl at adjust the pH 2-3. The separated aqueous layer was washed with isopropyl acetate. The combined organic layer was treated with sodium hydroxide solution (20.14 g) in water (200 mL) and stirred for 30 min. The separated aqueous layer was treated with magnesium acetate tetrahydrate (2.29 g) in water (5 mL) solution and stirred for 60 min. The reaction mixture was extracted with methylene dichloride (800 mL). The methylene dichloride was complete removed by distillation under vacuum below 40° C. to obtain the residue. The residue was diluted with methylene dichloride (50 mil) and stirred for 30 min. The organic solution was added into n-heptane (1500 mL) and stirred for 3 hours. The product was filtered and washed with n-heptane and dried in vacuum tray dryer at 25° C. to 30° C. for 3 hours. The product was sieved through 0.5 mm sieve and milled through jet-milled. The product was further dried in vacuum tray drier at 40° C. to 50° C. for 6 hours followed by drying at 55° C. to 65° C. for 40 hours to obtain substantially amorphous saroglitazar magnesium (I). The compound is characterized by x-ray power diffraction (FIG. 1).

While the present invention has been described in terms of its specific embodiments, certain modifications and equivalents will be apparent to those skilled in the art and are intended to be included within the scope of the present invention.

We claim:

1. A process for the preparation of a saroglitazar pharmaceutically acceptable salt of Formula (IB),

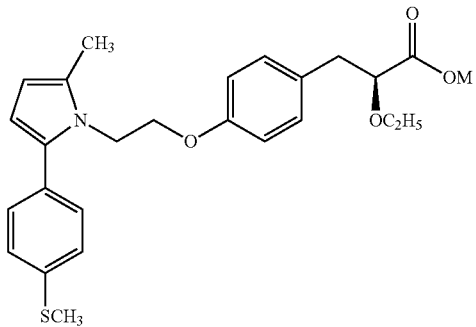
(IB)

wherein M is a pharmaceutically acceptable cation, the process comprising:
(a) reacting a hydroxy compound (A) with a mesylate compound (A1), in a mixture of cyclohexane and tetrahydrofuran in the presence of a base, to obtain alkoxy ester compound of Formula (II);

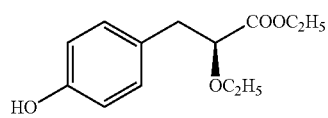
(A)

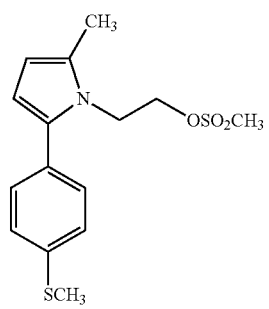
(A1)

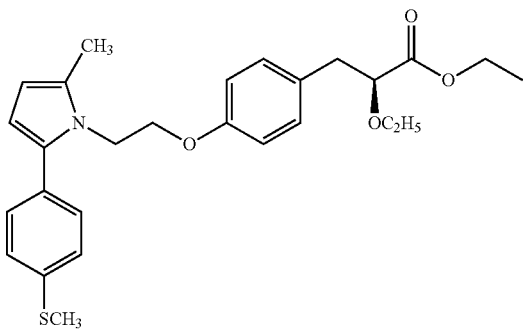
(II)

(b) hydrolyzing the alkoxy ester compound of Formula (II) using a base to obtain a compound of Formula (IB-1);

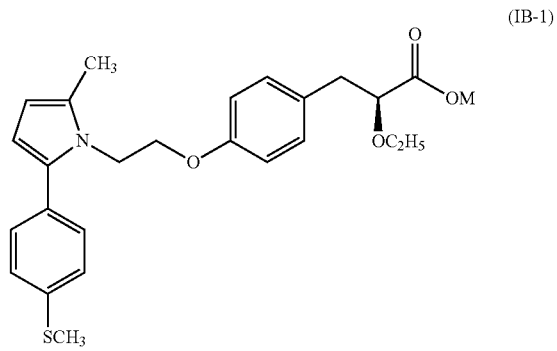
(IB-1)

wherein M is a pharmaceutically acceptable cation selected from sodium, potassium, lithium, calcium, barium, strontium, and zinc;
(c) neutralizing the compound of Formula (IB-1) with an acid to obtain a compound of Formula (IB-2):

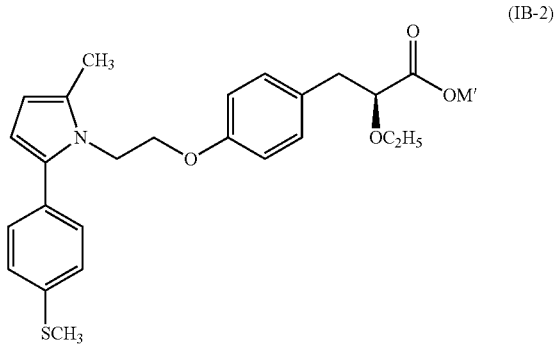
(IB-2)

wherein M' is hydrogen; and
(d) converting the compound of Formula (IB-2) to a compound of Formula (IB).

2. The process as claimed in claim 1, wherein the reaction of hydroxy compound (A) with mesylate compound (A1) is performed in the presence of a phase transfer catalyst.

3. The process as claimed in claim 1, wherein the acid in step (c) comprises one or more of hydrochloric acid, hydrobromic acid, sulfuric acid, nitric acid, phosphoric acid, acetic acid, trifluoroacetic acid, and formic acid.

4. The process as claimed in claim 1, wherein the base in step (b) comprises one or more of sodium hydroxide, potassium hydroxide, lithium hydroxide, calcium hydroxide, barium hydroxide, strontium hydroxide, zinc hydroxide, sodium carbonate, potassium carbonate, lithium carbonate, sodium bicarbonate, potassium bicarbonate, sodium hydride, potassium hydride, potassium tert-butoxide, and sodium pentoxide.

5. The process as claimed in claim 1, wherein in step (d) the pharmaceutically acceptable cation of Formula (IB) is selected from sodium, potassium, lithium, calcium, barium, magnesium, strontium, and zinc.

6. A process for the preparation of saroglitazar magnesium Formula (I),

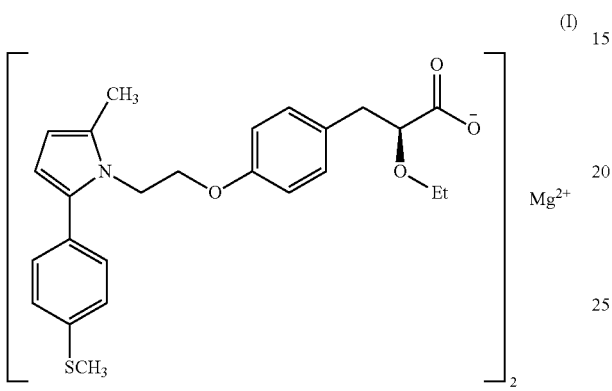

(I)

the process comprising:
(a) reacting a hydroxy compound (A) with a mesylate compound (A1), in a mixture of cyclohexane and tetrahydrofuran in the presence of a base, to obtain alkoxy ester compound of Formula (II);

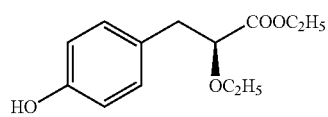

(A)

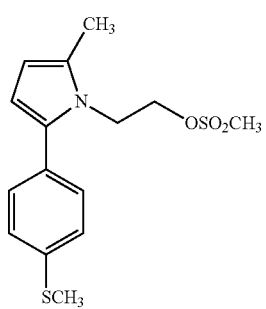

(A1)

(II)

(b) hydrolyzing the alkoxy ester compound of Formula (II) using a base to obtain a compound of Formula (IB);

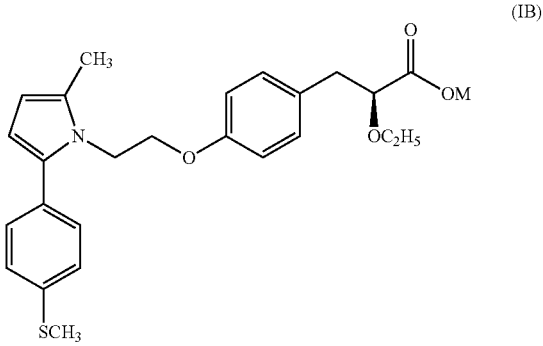

(IB)

wherein M is a pharmaceutically acceptable cation selected from sodium, potassium, lithium, calcium, barium, strontium, and zinc;
(c) neutralizing the compound of Formula (IB) with an acid to obtain a compound of Formula (IB-1):

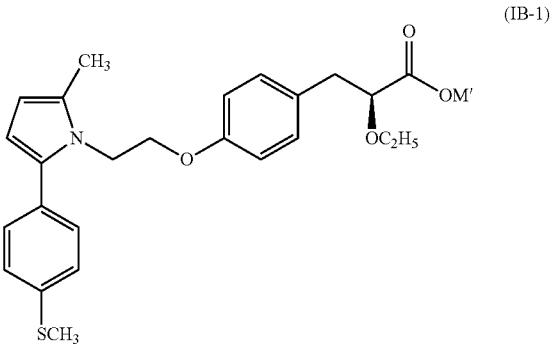 [SMILES: CCO[C@@H](Cc1ccc(OCCn2c(C)ccc2-c2ccc(SC)cc2)cc1)C(=O)O]

(IB-1)

wherein M' is hydrogen; and
(d) reacting the compound of Formula (IB-1) with a magnesium source to obtain the saroglitazar magnesium of Formula (I).

7. The process as claimed in claim 6, wherein the base in step (b) comprises one or more of sodium hydroxide, potassium hydroxide, lithium hydroxide, calcium hydroxide, barium hydroxide, strontium hydroxide, zinc hydroxide, sodium carbonate, potassium carbonate, lithium carbonate, sodium bicarbonate, potassium bicarbonate, sodium hydride, potassium hydride, potassium tert-butoxide, and sodium pentoxide.

8. The process as claimed in claim 6, wherein the magnesium source in step (d) comprises one or more of magnesium hydroxide, magnesium methoxide, magnesium acetate, magnesium chloride, and magnesium metal.

9. The process as claimed in claim 6, further comprising:
extracting the saroglitazar magnesium in step (d) with one or more organic solvents;
removing the organic solvent to obtain a residue;
treating the residue with one or more organic solvents to obtain a solution;
adding the solution into an anti-solvent to obtain saroglitazar magnesium; and
filtering and drying the saroglitazar magnesium, and thereafter milling the saroglitazar magnesium.

10. The process as claimed in claim 9, wherein the organic solvent comprises one or more of: methylene dichloride, ethylene dichloride, chlorobenzene, toluene, xylene, and ethylbenzene.

11. The process as claimed in claim 9, wherein the anti-solvent comprises one or more of: pentane, hexane, heptane, cyclohexane, tetrahydrofuran, 1,4-dioxane, diisopropyl ether, diethyl ether, and methyl tertbutyl ether.

12. The process as claimed in claim 9, wherein the anti-solvent is diluted with one or more solvents comprising an ester selected from ethyl acetate, isopropyl acetate, n-butyl acetate, t-butyl acetate, and isobutyl acetate.

13. A process for the preparation of saroglitazar magnesium of Formula (I),

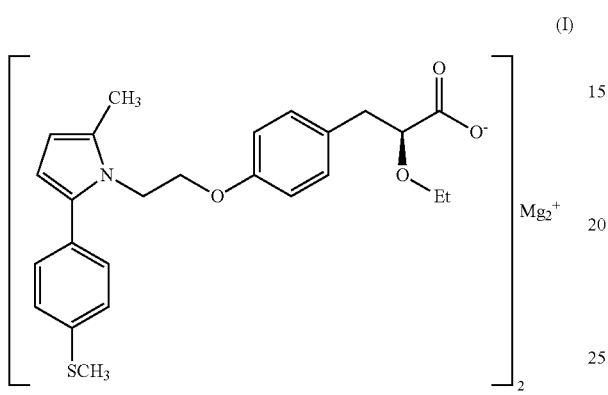

the process comprising:
(a) reacting a hydroxy compound (A) with a mesylate compound (A1), in a mixture of cyclohexane and tetrahydrofuran in the presence of a base, to obtain alkoxy ester compound of Formula (II);

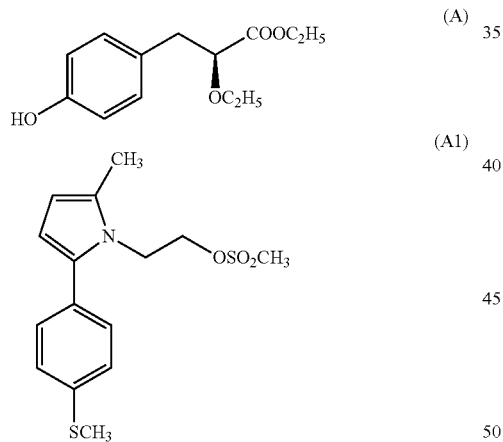

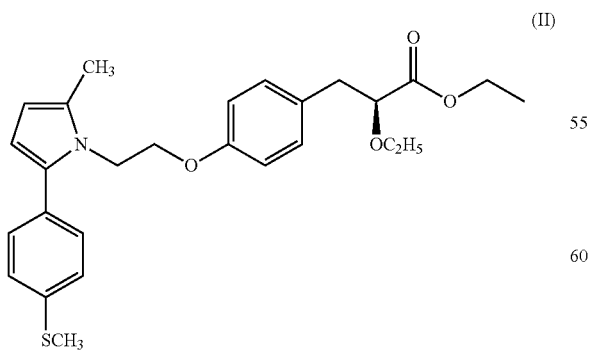

(b) hydrolyzing the alkoxy ester compound of Formula (II) with a base to obtain a compound of Formula (IB);

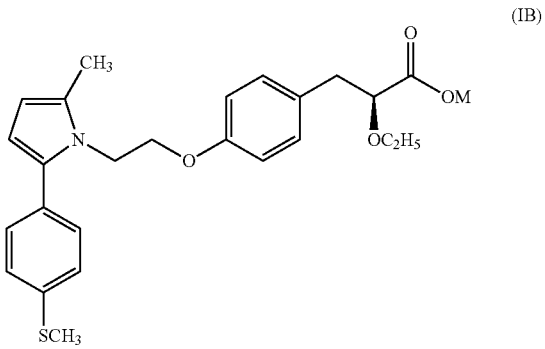

wherein M is a pharmaceutically acceptable cation selected from sodium, potassium, lithium, calcium, barium, strontium, and zinc;

(c) neutralizing the compound of Formula (IB) with an acid to obtain a compound of Formula (IB-1)

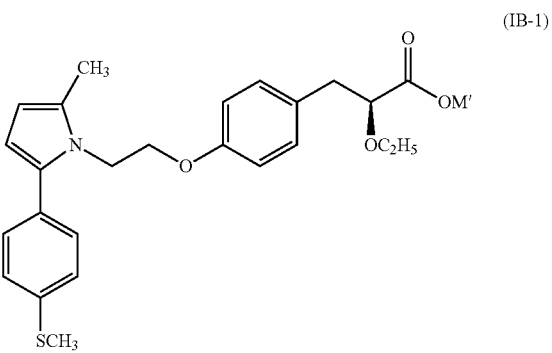

wherein M' is hydrogen; and (d) reacting the compound of Formula (IB-1) with an organic amine to obtain a compound of Formula (IC);

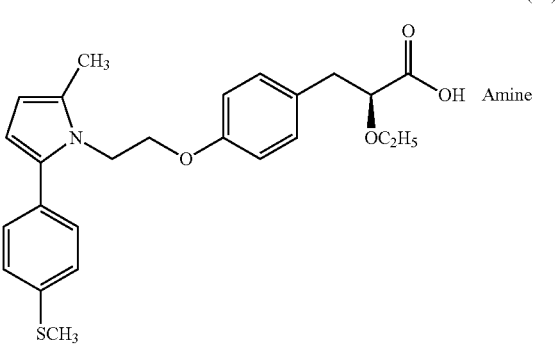

(e) converting the compound of Formula (IC) to a compound of Formula (IB-2):

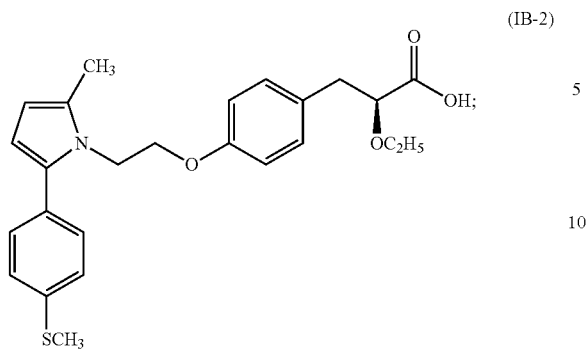

and (f) reacting the compound of Formula (IB-2) with a magnesium source to obtain the saroglitazar magnesium of Formula (I).

14. The process as claimed in claim 13, wherein the organic amine in step (d) comprises one or more of ammonia, methylamine, dimethylamine, ethylamine, diethylamine, 1,2-ethanediamine, n-propyl amine, isopropylamine, diisopropylamine, N-methyl isopropylamine, butylamine, t-butyl amine, 2-butamine, 1,2-ethanediamine, N-methylglucamine, N,N,N-trimethylethanol- amine hydroxide (choline), tromethamine, cyclohexylamine, N-methylcyclohexylamine, guanidine, N-(4-aminobutyl)guanidine dicyclohexylamine, benzenemethanamine, ethanolamine, diethanolamine, tris(hydroxymethyl)methylamine, hydroxylamine, methanaminium, benzylamine, N-methylbenzylamine, N-ethyl benzylamine, (R,S)-1-phenylethylamine, (S)-1-phenylethylamine, (R)-1-phenylethylamine, 4-methoxybenzyl amine, pyrrolidine, piperidine, piperazine, morpholine, 2-aminopyrimidine, L-alanine, L-lysine, D-lysine, L-arginine, L-histidine, L-threonine, 2-thiopheneethanamine, (2S)-3,3-dimethyl-2-butanamine, cyclopentanamine, and cycloheptanamine.

15. A process for the preparation of saroglitazar magnesium of Formula (I),

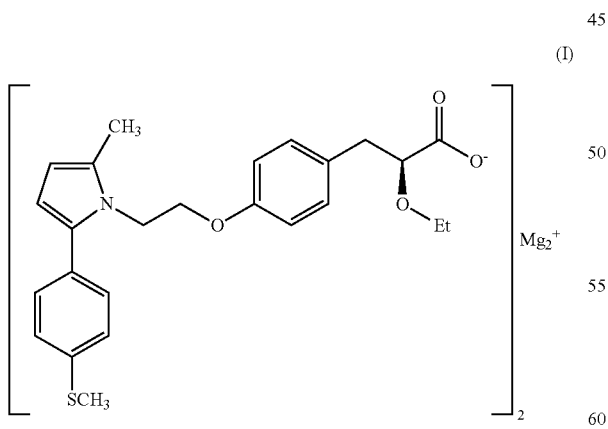

the process comprising:

(a) reacting 2-bromo-1-(4-(methylthio)phenyl)ethanone (E1) with methyl acetoacetate in one or more of organic solvents in the presence of a base to obtain a compound (D1);

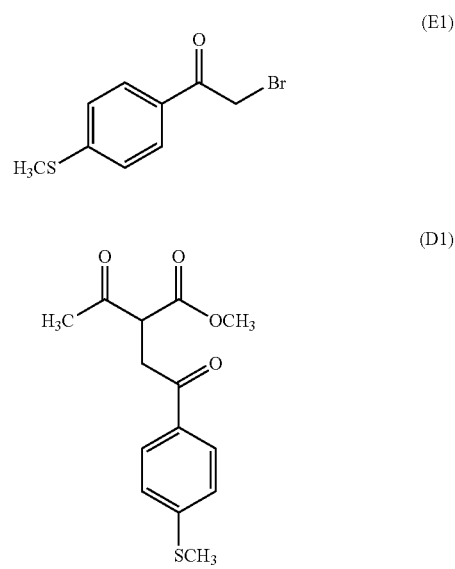

(b) hydrolyzing the compound (D1) in-situ with a base followed by decarboxylation to obtain a compound (C1);

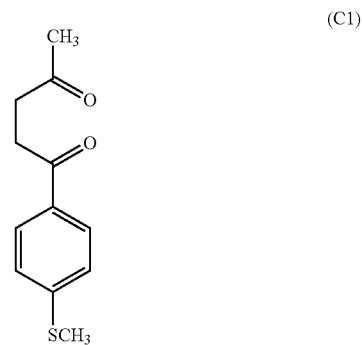

(c) reacting the compound (C1) in-situ with ethanolamine under Paal-Knoor conditions in the presence of an acid to obtain a compound (B1);

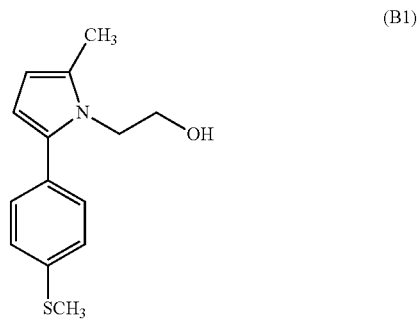 [SMILES: CSc1ccc(-c2ccc(C)n2CCO)cc1]

(d) reacting the compound (B1) in-situ with methane sulphonyl chloride in the presence of a base to obtain mesylate compound (A1);

43

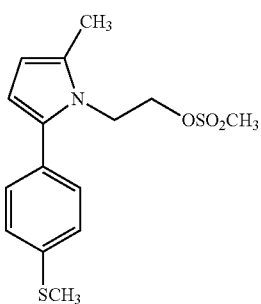
(A1)

(e) reacting the mesylate compound (A1) in-situ with a hydroxy compound (A) in the presence of a base to obtain an alkoxy ester compound of Formula (II);

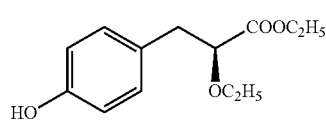
(A)

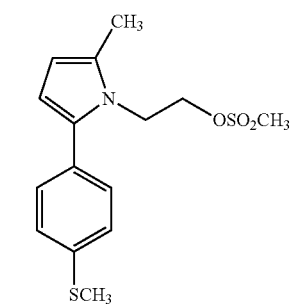
(A1)

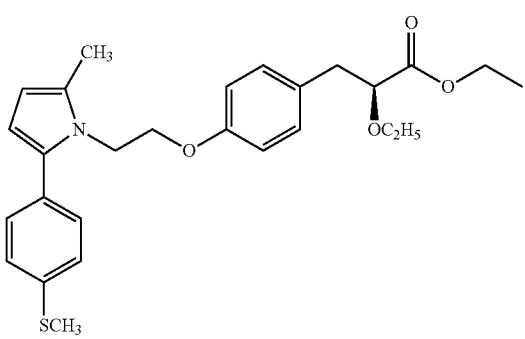
(II)

(f) hydrolyzing the alkoxy ester compound of Formula (II) in-situ using a base to obtain a compound of Formula (IB);

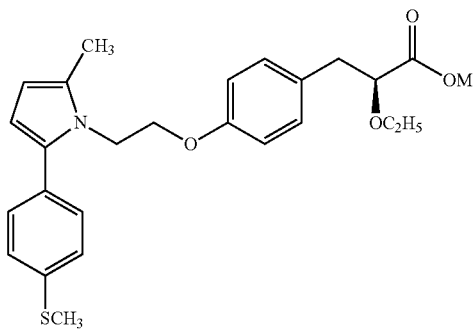
(IB)

44 wherein M is a pharmaceutically acceptable cation selected from sodium, potassium, lithium, calcium, barium, strontium and zinc;

(g) neutralizing the compound of Formula (IB) to obtain the compound of Formula (IB-1):

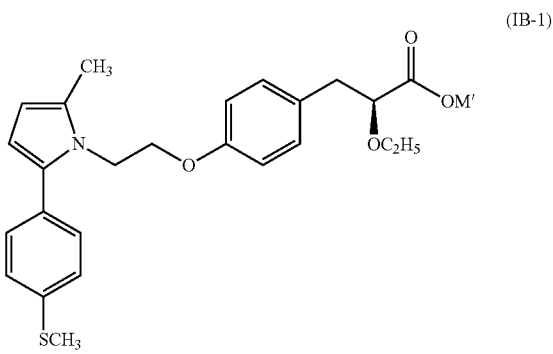
(IB-1)

wherein M' is hydrogen; and (h) reacting the compound of Formula (IB-1) with a magnesium source to obtain the saroglitazar magnesium of Formula (I), wherein the process does not involve isolation of intermediates.

16. The process as claimed in claim 15, wherein the organic solvent in step (a) comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; or chlorinated solvents selected from methylene dichloride, ethylene dichloride, chlorobenzene, chloroform, and carbon tetrachloride.

17. The process as claimed in claim 15, wherein the base in step (a) comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, sodium methoxide, potassium tert-butoxide, and sodium pentoxide.

18. The process as claimed in claim 15, wherein the acid in step (c) comprises one or more of acetic acid, hydrochloric acid, sulfuric acid, formic acid, hydrobromic acid, trifluoroacetic acid, and pivalic acid.

19. The process as claimed in claim 15, wherein the base in step (d) comprises one or more of alkali metal hydroxides selected from sodium hydroxide, potassium hydroxide, and lithium hydroxide; alkali metal carbonates selected from sodium carbonate, potassium carbonate, and cesium carbonate; alkali metal bicarbonates selected from sodium bicarbonate and potassium bicarbonate; ammonia or its aqueous solution; or an organic base selected from methyl amine, ethyl amine, TEA, TBA, DIPA, DIPEA, pyridine, piperidine, morpholine, DBU, DABCO and DBN.

20. The process as claimed in claim 9, wherein the milling comprises one or more of ball mill, roller mill, gyratory mill, multi-mill, or jet-mill.

* * * * *